(12) United States Patent
Posey et al.

(10) Patent No.: US 12,232,725 B2
(45) Date of Patent: *Feb. 25, 2025

(54) SURGICAL STAPLER WITH SLOPED STAPLE DECK FOR VARYING TISSUE COMPRESSION

(71) Applicant: Cilag GmbH International, Zug (CH)

(72) Inventors: Ryan P. Posey, Cincinnati, OH (US); Nicholas D. Courtwright, Villa Hills, KY (US); Stephen D. Geresy, West Chester, OH (US); Kevin D. Sackett, Independence, KY (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/323,159

(22) Filed: May 24, 2023

(65) Prior Publication Data
US 2023/0309998 A1   Oct. 5, 2023

Related U.S. Application Data

(63) Continuation of application No. 16/234,740, filed on Dec. 28, 2018, now Pat. No. 11,701,109.

(51) Int. Cl.
*A61B 17/072* (2006.01)

(52) U.S. Cl.
CPC .. *A61B 17/072* (2013.01); *A61B 2017/07221* (2013.01); *A61B 2017/07257* (2013.01);
(Continued)

(58) Field of Classification Search
CPC ........ A61B 17/072; A61B 2017/07221; A61B 2017/07257; A61B 2017/07264; A61B 2017/07271; A61B 2017/07285
(Continued)

(56) References Cited

U.S. PATENT DOCUMENTS

| 4,805,823 A | 2/1989 | Rothfuss |
| 5,156,315 A | 10/1992 | Green et al. |

(Continued)

FOREIGN PATENT DOCUMENTS

| AU | 2010206646 A1 * | 7/2011 | ........... A61B 17/064 |
| CN | 2500264 Y | 7/2002 | |

(Continued)

OTHER PUBLICATIONS

Chinese first Office Action and Search Report dated Oct. 21, 2023, for Application No. 201980093207.9, 9 pages.
(Continued)

*Primary Examiner* — Robert F Long
(74) *Attorney, Agent, or Firm* — Frost Brown Todd LLP

(57) ABSTRACT

A cartridge for use with a surgical instrument includes a curved body and a deck defined by the curved body and configured to clamp tissue against an anvil. A plurality of staple openings is formed in the deck and is configured to house a plurality of staples. An arcuate slot is formed in the deck and is configured to slidably receive a cutting member therethrough. The deck includes a sloped deck portion that slopes away from the arcuate slot in a direction transverse to a length of the arcuate slot. The sloped deck portion is configured to provide varied compression of tissue across a width of the deck.

20 Claims, 13 Drawing Sheets

(52) U.S. Cl.
CPC .............. *A61B 2017/07264* (2013.01); *A61B 2017/07271* (2013.01); *A61B 2017/07285* (2013.01)

(58) Field of Classification Search
USPC .................. 606/139, 142, 143, 205–208; 227/175.1–182.1, 8, 19
See application file for complete search history.

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,415,334 A | 5/1995 | Williamson, IV et al. | |
| 5,441,193 A | 8/1995 | Gravener | |
| 5,452,837 A | 9/1995 | Williamson, IV et al. | |
| 5,465,895 A | 11/1995 | Knodel et al. | |
| 5,533,661 A | 7/1996 | Main et al. | |
| 5,588,579 A | 12/1996 | Schnut et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,876,401 A | 3/1999 | Schulze et al. | |
| 5,878,193 A | 3/1999 | Wang et al. | |
| 5,893,863 A | 4/1999 | Yoon | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton, IV et al. | |
| 6,978,922 B2 | 12/2005 | Bilotti et al. | |
| 6,988,650 B2 | 1/2006 | Schwemberger et al. | |
| 7,000,818 B2 | 2/2006 | Shelton, IV et al. | |
| 7,070,083 B2 | 7/2006 | Jankowski | |
| 7,134,587 B2 | 11/2006 | Schwemberger et al. | |
| 7,143,923 B2 | 12/2006 | Shelton, IV et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,303,108 B2 | 12/2007 | Shelton, IV | |
| RE40,237 E | 4/2008 | Bilotti et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,398,908 B2 | 7/2008 | Holsten et al. | |
| 7,404,508 B2 | 7/2008 | Smith et al. | |
| 7,422,138 B2 | 9/2008 | Bilotti et al. | |
| 7,434,715 B2 | 10/2008 | Shelton, IV et al. | |
| 7,434,717 B2 | 10/2008 | Shelton, IV et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,794,475 B2 | 9/2010 | Hess et al. | |
| 7,806,891 B2 | 10/2010 | Nowlin et al. | |
| 8,091,756 B2 | 1/2012 | Viola | |
| 8,141,762 B2 | 3/2012 | Bedi et al. | |
| 8,210,411 B2 | 7/2012 | Yates et al. | |
| 8,272,552 B2 | 9/2012 | Holsten et al. | |
| 8,317,070 B2 | 11/2012 | Hueil et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,540,132 B2 | 9/2013 | Marczyk et al. | |
| 8,573,461 B2 | 11/2013 | Shelton, IV et al. | |
| 8,573,465 B2 | 11/2013 | Shelton, IV | |
| 8,579,178 B2 | 11/2013 | Holsten et al. | |
| 8,579,990 B2 | 11/2013 | Priewe | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,910,847 B2 | 12/2014 | Nalagatla et al. | |
| 8,967,446 B2 | 3/2015 | Beardsley et al. | |
| 8,992,060 B2 | 4/2015 | Dassanayake et al. | |
| 8,998,060 B2 | 4/2015 | Bruewer et al. | |
| 9,016,539 B2 | 4/2015 | Kostrzewski et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,211,120 B2 | 12/2015 | Scheib et al. | |
| 9,254,131 B2 | 2/2016 | Soltz et al. | |
| 9,289,207 B2 | 3/2016 | Shelton, IV | |
| 9,301,759 B2 | 4/2016 | Spivey et al. | |
| 9,314,246 B2 | 4/2016 | Shelton, IV et al. | |
| 9,351,724 B2 | 5/2016 | Penna | |
| 9,364,217 B2 | 6/2016 | Kostrzewski et al. | |
| 9,364,225 B2 | 6/2016 | Sniffin et al. | |
| 9,393,018 B2 | 7/2016 | Wang et al. | |
| 9,398,911 B2 | 7/2016 | Auld et al. | |
| 9,463,022 B2 | 10/2016 | Swayze et al. | |
| 9,492,170 B2 | 11/2016 | Bear et al. | |
| 9,498,222 B2 | 11/2016 | Scheib et al. | |
| 9,517,065 B2 | 12/2016 | Simms et al. | |
| 9,532,783 B2 | 1/2017 | Swayze et al. | |
| 9,572,573 B2 | 2/2017 | Scheib et al. | |
| 9,572,574 B2 | 2/2017 | Shelton, IV et al. | |
| 9,597,081 B2 | 3/2017 | Swayze et al. | |
| 9,597,082 B2 | 3/2017 | Stokes et al. | |
| 9,622,746 B2 | 4/2017 | Simms et al. | |
| 9,668,734 B2 | 6/2017 | Kostrzewski et al. | |
| 9,713,469 B2 | 7/2017 | Leimbach et al. | |
| 9,717,497 B2 | 8/2017 | Zerkle et al. | |
| 9,724,100 B2 | 8/2017 | Scheib et al. | |
| 9,737,301 B2 | 8/2017 | Baber et al. | |
| 9,750,503 B2 | 9/2017 | Milliman | |
| 9,757,133 B2 | 9/2017 | Latimer et al. | |
| 9,795,379 B2 | 10/2017 | Leimbach et al. | |
| 9,808,248 B2 | 11/2017 | Hoffman | |
| 9,833,241 B2 * | 12/2017 | Huitema .............. | A61B 17/072 |
| 9,839,421 B2 | 12/2017 | Zerkle et al. | |
| 9,844,369 B2 | 12/2017 | Huitema et al. | |
| 9,848,871 B2 | 12/2017 | Harris et al. | |
| 9,848,877 B2 | 12/2017 | Shelton, IV et al. | |
| 9,867,615 B2 | 1/2018 | Fanelli et al. | |
| 9,907,552 B2 | 3/2018 | Measamer et al. | |
| 9,913,642 B2 | 3/2018 | Leimbach et al. | |
| 9,936,949 B2 | 4/2018 | Measamer et al. | |
| 9,936,954 B2 | 4/2018 | Shelton, IV et al. | |
| 9,943,310 B2 | 4/2018 | Harris et al. | |
| 9,999,408 B2 | 6/2018 | Boudreaux et al. | |
| 10,045,780 B2 | 8/2018 | Adams et al. | |
| 10,076,325 B2 | 9/2018 | Huang et al. | |
| 10,080,565 B2 | 9/2018 | Pastorelli et al. | |
| 10,092,292 B2 | 10/2018 | Boudreaux et al. | |
| D833,010 S | 11/2018 | Harris et al. | |
| 10,123,798 B2 | 11/2018 | Baxter, III et al. | |
| D836,198 S | 12/2018 | Harris et al. | |
| D836,199 S | 12/2018 | Schowalter et al. | |
| 10,194,912 B2 | 2/2019 | Scheib et al. | |
| 10,258,330 B2 | 4/2019 | Shelton, IV et al. | |
| 10,285,705 B2 | 5/2019 | Shelton, IV et al. | |
| 10,314,580 B2 | 6/2019 | Scheib et al. | |
| 10,349,939 B2 | 7/2019 | Shelton, IV et al. | |
| 10,456,134 B2 | 10/2019 | DiNardo et al. | |
| 10,470,768 B2 | 11/2019 | Harris et al. | |
| 10,478,189 B2 | 11/2019 | Bear et al. | |
| 10,485,548 B2 | 11/2019 | Miller et al. | |
| 10,507,032 B2 | 12/2019 | Demmy et al. | |

(56) References Cited

U.S. PATENT DOCUMENTS

| | | | |
|---|---|---|---|
| 10,542,981 B2 | 1/2020 | Miller et al. |
| 10,603,041 B2 | 3/2020 | Miller et al. |
| 10,687,812 B2 | 6/2020 | Shelton, IV et al. |
| 10,758,231 B2 | 9/2020 | Harris et al. |
| 10,806,451 B2 | 10/2020 | Harris et al. |
| D901,686 S | 11/2020 | Barton et al. |
| D903,115 S | 11/2020 | Zeiner et al. |
| 10,905,424 B2 | 2/2021 | Bakos et al. |
| 10,980,542 B2 | 4/2021 | Miller et al. |
| D922,576 S | 6/2021 | Schellin et al. |
| 11,033,269 B2 | 6/2021 | Vendely et al. |
| 11,039,834 B2* | 6/2021 | Harris ............... A61B 17/072 |
| D926,317 S | 7/2021 | Posey et al. |
| D926,318 S | 7/2021 | Posey et al. |
| 11,103,243 B2 | 8/2021 | Bakos et al. |
| 11,116,505 B2 | 9/2021 | Vendely et al. |
| D932,621 S | 10/2021 | Ridgley et al. |
| D933,220 S | 10/2021 | Tate et al. |
| 11,166,724 B2 | 11/2021 | McGiveron et al. |
| 11,166,725 B2 | 11/2021 | Vendely et al. |
| 11,202,628 B2 | 12/2021 | Posey et al. |
| 11,272,935 B2 | 3/2022 | Bakos et al. |
| 11,432,817 B2 | 9/2022 | Barton et al. |
| 11,701,109 B2 | 7/2023 | Posey et al. |
| 2002/0143346 A1 | 10/2002 | McGuckin, Jr. et al. |
| 2004/0004105 A1 | 1/2004 | Jankowski |
| 2005/0139629 A1 | 6/2005 | Schwemberger et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2007/0034667 A1 | 2/2007 | Holsten et al. |
| 2007/0034668 A1 | 2/2007 | Holsten et al. |
| 2007/0114261 A1 | 5/2007 | Ortiz et al. |
| 2007/0131732 A1 | 6/2007 | Holsten et al. |
| 2008/0169328 A1 | 7/2008 | Shelton |
| 2008/0169330 A1 | 7/2008 | Shelton et al. |
| 2008/0169333 A1 | 7/2008 | Shelton et al. |
| 2010/0213238 A1 | 8/2010 | Farascioni et al. |
| 2011/0068147 A1 | 3/2011 | Racenet et al. |
| 2012/0029272 A1* | 2/2012 | Shelton, IV ....... A61B 17/3431 600/37 |
| 2012/0074198 A1 | 3/2012 | Huitema et al. |
| 2012/0168487 A1 | 7/2012 | Holsten et al. |
| 2012/0241493 A1 | 9/2012 | Baxter, III et al. |
| 2012/0325893 A1 | 12/2012 | Pastorelli et al. |
| 2013/0026209 A1 | 1/2013 | Mozdzierz et al. |
| 2013/0068816 A1 | 3/2013 | Vasudevan et al. |
| 2013/0075447 A1 | 3/2013 | Weisenburgh et al. |
| 2013/0105549 A1 | 5/2013 | Holsten et al. |
| 2013/0119109 A1 | 5/2013 | Farascioni et al. |
| 2013/0161375 A1 | 6/2013 | Huitema et al. |
| 2013/0206813 A1 | 8/2013 | Nalagatla |
| 2014/0158747 A1 | 6/2014 | Measamer et al. |
| 2014/0166728 A1 | 6/2014 | Swayze et al. |
| 2014/0224686 A1 | 8/2014 | Aronhalt et al. |
| 2014/0239037 A1 | 8/2014 | Boudreaux et al. |
| 2015/0083772 A1 | 3/2015 | Miller et al. |
| 2015/0108198 A1 | 4/2015 | Estrella |
| 2015/0282825 A1 | 10/2015 | Trees et al. |
| 2015/0289872 A1 | 10/2015 | Chen et al. |
| 2015/0297235 A1 | 10/2015 | Harris et al. |
| 2015/0297236 A1 | 10/2015 | Harris et al. |
| 2015/0351758 A1 | 12/2015 | Shelton, IV et al. |
| 2016/0058441 A1 | 3/2016 | Morgan et al. |
| 2016/0089146 A1 | 3/2016 | Harris et al. |
| 2016/0089149 A1 | 3/2016 | Harris et al. |
| 2016/0106427 A1 | 4/2016 | Shelton, IV et al. |
| 2016/0120544 A1 | 5/2016 | Shelton, IV et al. |
| 2016/0120545 A1 | 5/2016 | Shelton, IV et al. |
| 2016/0278774 A1 | 9/2016 | Shelton, IV et al. |
| 2017/0027571 A1 | 2/2017 | Nalagatla et al. |
| 2017/0049444 A1 | 2/2017 | Schellin et al. |
| 2017/0055980 A1 | 3/2017 | Vendely et al. |
| 2017/0055981 A1 | 3/2017 | Vendely et al. |
| 2017/0055982 A1 | 3/2017 | Zeiner et al. |
| 2017/0055986 A1 | 3/2017 | Harris et al. |
| 2017/0056016 A1 | 3/2017 | Barton et al. |
| 2017/0056017 A1 | 3/2017 | Vendely et al. |
| 2017/0056018 A1 | 3/2017 | Zeiner et al. |
| 2017/0086823 A1 | 3/2017 | Leimbach et al. |
| 2017/0086837 A1 | 3/2017 | Vendely et al. |
| 2017/0086842 A1 | 3/2017 | Shelton, IV et al. |
| 2017/0105725 A1 | 4/2017 | Scheib et al. |
| 2017/0105728 A1 | 4/2017 | Scheib et al. |
| 2017/0189022 A1 | 7/2017 | Adams et al. |
| 2017/0281164 A1 | 10/2017 | Harris et al. |
| 2017/0281177 A1 | 10/2017 | Harris et al. |
| 2017/0281188 A1 | 10/2017 | Shelton, IV et al. |
| 2018/0125487 A1 | 5/2018 | Beardsley |
| 2018/0132848 A1 | 5/2018 | Miller et al. |
| 2018/0168627 A1 | 6/2018 | Weaner et al. |
| 2018/0168632 A1 | 6/2018 | Harris et al. |
| 2018/0235610 A1 | 8/2018 | Harris et al. |
| 2018/0235611 A1 | 8/2018 | Harris et al. |
| 2018/0235619 A1 | 8/2018 | Harris et al. |
| 2018/0368836 A1 | 12/2018 | Auld et al. |
| 2018/0368839 A1* | 12/2018 | Shelton, IV ..... A61B 17/07207 |
| 2019/0000481 A1 | 1/2019 | Harris et al. |
| 2019/0059892 A1 | 2/2019 | Miller et al. |
| 2019/0059893 A1 | 2/2019 | Miller et al. |
| 2019/0175173 A1 | 6/2019 | Harris et al. |
| 2019/0261982 A1 | 8/2019 | Holsten |
| 2020/0015815 A1 | 1/2020 | Harris et al. |
| 2020/0205811 A1 | 7/2020 | Posey et al. |
| 2020/0205822 A1 | 7/2020 | Heupel et al. |
| 2020/0405295 A1 | 12/2020 | Shelton, IV et al. |
| 2021/0186494 A1 | 6/2021 | Shelton, IV et al. |
| 2022/0000479 A1 | 1/2022 | Shelton, IV et al. |
| 2022/0047265 A1 | 2/2022 | Miller et al. |

FOREIGN PATENT DOCUMENTS

| | | |
|---|---|---|
| CN | 102755180 A | 10/2012 |
| CN | 103431886 A | 12/2013 |
| CN | 103829983 A | 6/2014 |
| CN | 104490441 A | 4/2015 |
| CN | 107847229 A | 3/2018 |
| CN | 107847230 A | 3/2018 |
| CN | 108348231 A | 7/2018 |
| EP | 1316290 A2 | 6/2003 |
| EP | 3 135 219 A1 | 3/2017 |
| EP | 3 225 196 A2 | 10/2017 |
| EP | 3 320 860 A1 | 5/2018 |
| JP | S60-139240 A | 7/1985 |
| JP | 2014-171866 A | 9/2014 |
| JP | 2017-511220 A | 4/2017 |
| JP | 2018-525140 A | 9/2018 |
| WO | WO-2016144689 A1 * | 9/2016 ........... A61B 17/068 |
| WO | WO 2018/152083 A1 | 8/2018 |

OTHER PUBLICATIONS

Brazil Office Action dated Jan. 24, 2022, for Application No. 112019009661-2, 4 pages.

Chinese Office Action and Search report dated Sep. 17, 2021, for Application No. 201780070636.5, 12 pages.

European Search Report and Written Opinion dated Mar. 14, 2018, for Application No. 17201387.2, 12 pages.

European Search Report and Written Opinion dated Mar. 9, 2020, for Application No. 19219447.0, 18 pages.

Indian Office Action dated Jun. 24, 2021, for Application No. 201917018408, 5 pages.

Indian Office Action dated Jan. 11, 2023, for Application No. 202117027996, 7 pages.

International Search Report and Written Opinion dated Aug. 8, 2017, for International Application No. PCT/US2017/035113, 15 pages.

International Search Report and Written Opinion dated Feb. 27, 2020, for International Application No. PCT/IB2019/060543, 20 pages.

Japanese Notification of Reasons for Refusal dated Jul. 30, 2021, for Application No. 2019-524971, 6 pages.

(56) References Cited

OTHER PUBLICATIONS

U.S. Appl. No. 62/209,041, entitled "Method and Apparatus for Applying a Buttress to End Effector of a Surgical Stapler," filed Aug. 24, 2015.
European Examination Report dated Dec. 11, 2023 for Application No. EP 19219447.0, 5 pgs.
Japanese Office Action, Notification of Reasons for Refusal, dated Sep. 5, 2023 for Application No. JP 2021-537830, 7 pgs.
Japanese Final Office Action dated Mar. 19, 2024, for Application No. JP 2021-537830, 5 pgs.

* cited by examiner

SURGICAL STAPLER WITH SLOPED STAPLE DECK FOR VARYING TISSUE COMPRESSION

This application is a continuation of U.S. patent application Ser. No. 16/234,740, entitled "Surgical Stapler With Sloped Staple Deck For Varying Tissue Compression," filed Dec. 28, 2018, issued as U.S. Pat. No. 11,701,109 on Jul. 18, 2023.

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
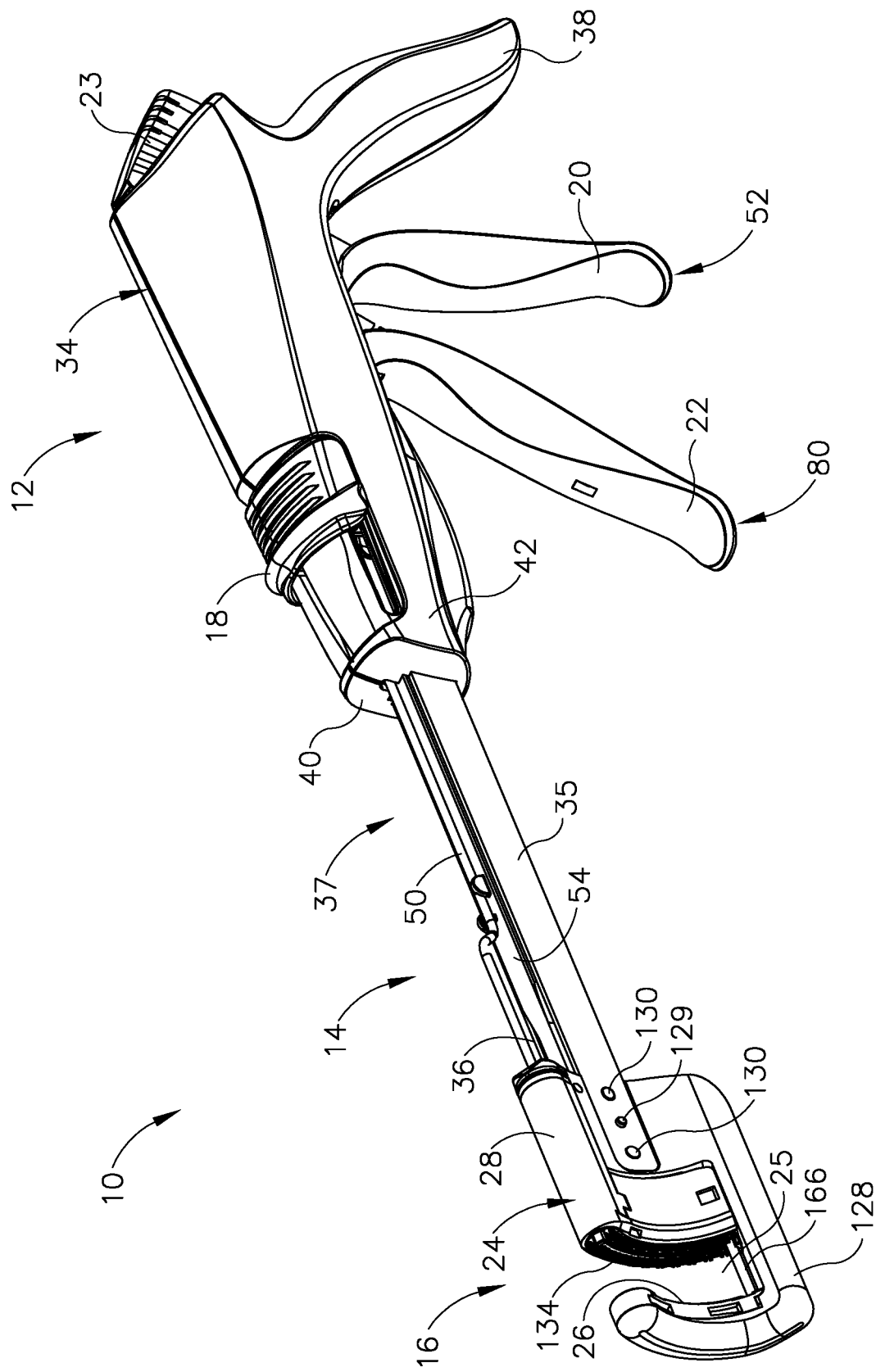
FIG. 1A depicts a right front perspective view of an exemplary surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

As used herein, the terms "about," "approximately," and the like in connection with any numerical values or ranges of values are intended to encompass the exact value(s) referenced, as well as a suitable dimensional tolerance that enables the referenced feature or combination of features to function for the intended purpose described herein.

I. Exemplary Surgical Stapler

FIGS. 1A-1D depict an exemplary surgical stapler (10) that includes a handle assembly (12), a shaft assembly (14) extending distally from handle assembly (12), and an end effector (16) at a distal end of shaft assembly (14). It should be understood that terms such as "proximal," "distal," "right," and "left" are used herein with reference to a clinician gripping handle assembly (12) of surgical stapler (10). Thus, end effector (16) is distal with respect to the relatively proximal handle assembly (12). Except as otherwise described herein, surgical stapler (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; and/or U.S. Pat. Pub. No. 2017/0027571 entitled "Surgical Instrument Comprising Systems for Assuring the Proper Sequential Operation of the Surgical Instrument," published on Feb. 2, 2017, issued as U.S. Pat. No. 10,194,913 on Feb. 5, 2019, the disclosure of which is incorporated by reference herein.

Figure 1B:
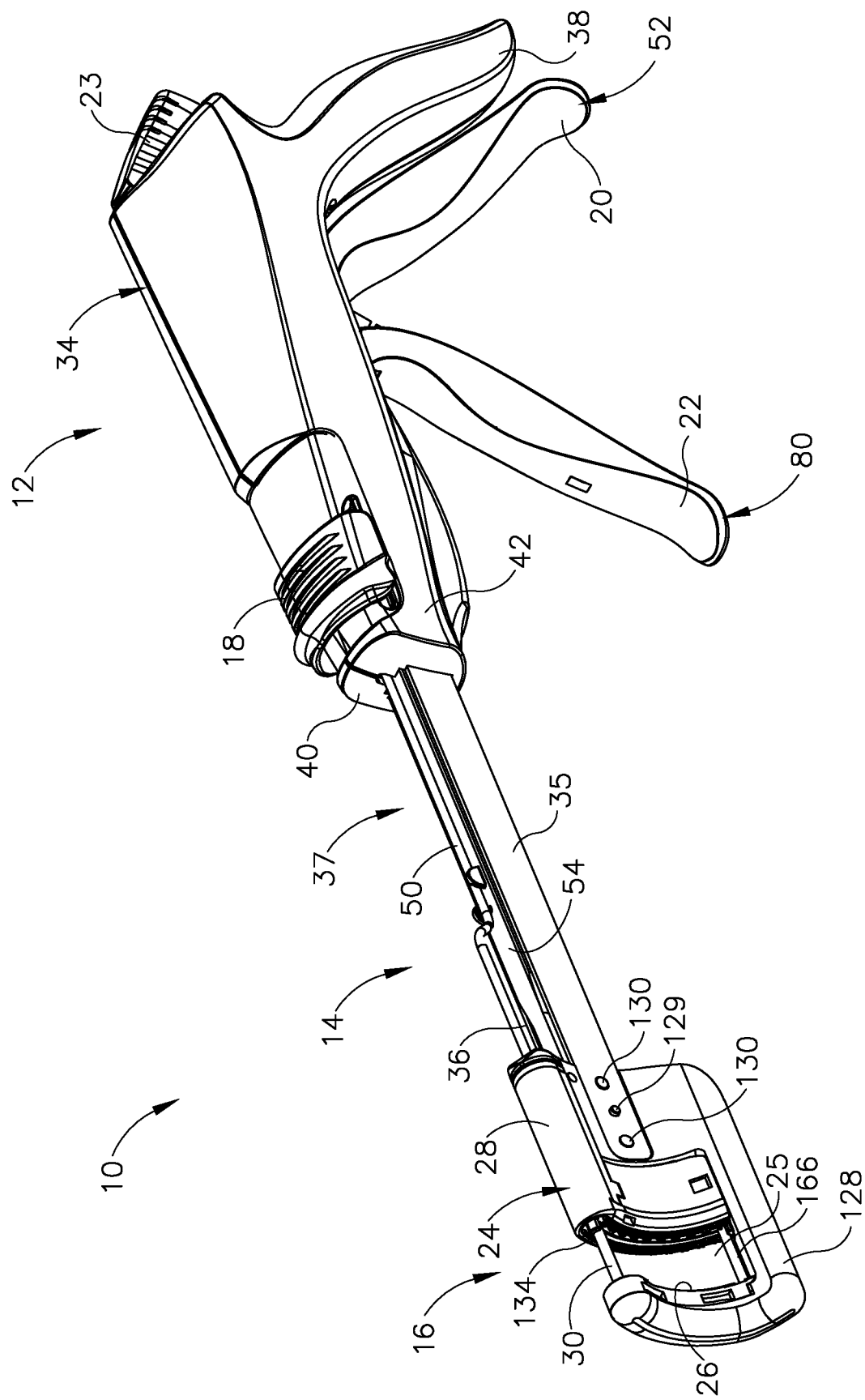
FIG. 1B depicts a right front perspective view of the surgical stapling instrument of FIG. 1A with the pin actuation mechanism in a closed position and the staple cartridge in the open position.
Figure 1C:
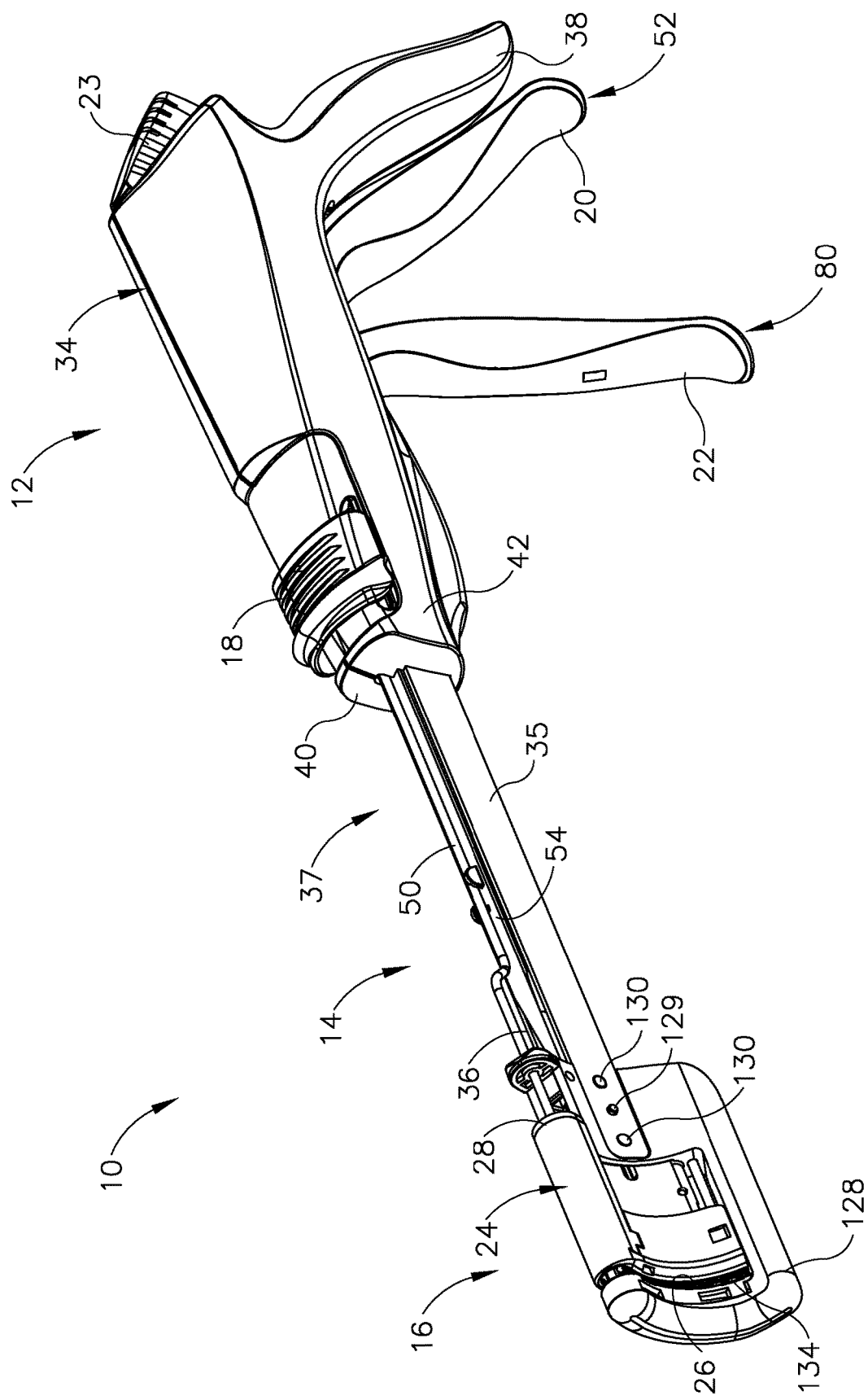
FIG. 1C depicts a right front perspective view of the surgical stapling instrument of FIG. 1A with the pin actuation mechanism in the closed position and the staple cartridge in a closed position via actuation of a closure mechanism.
Figure 1D:
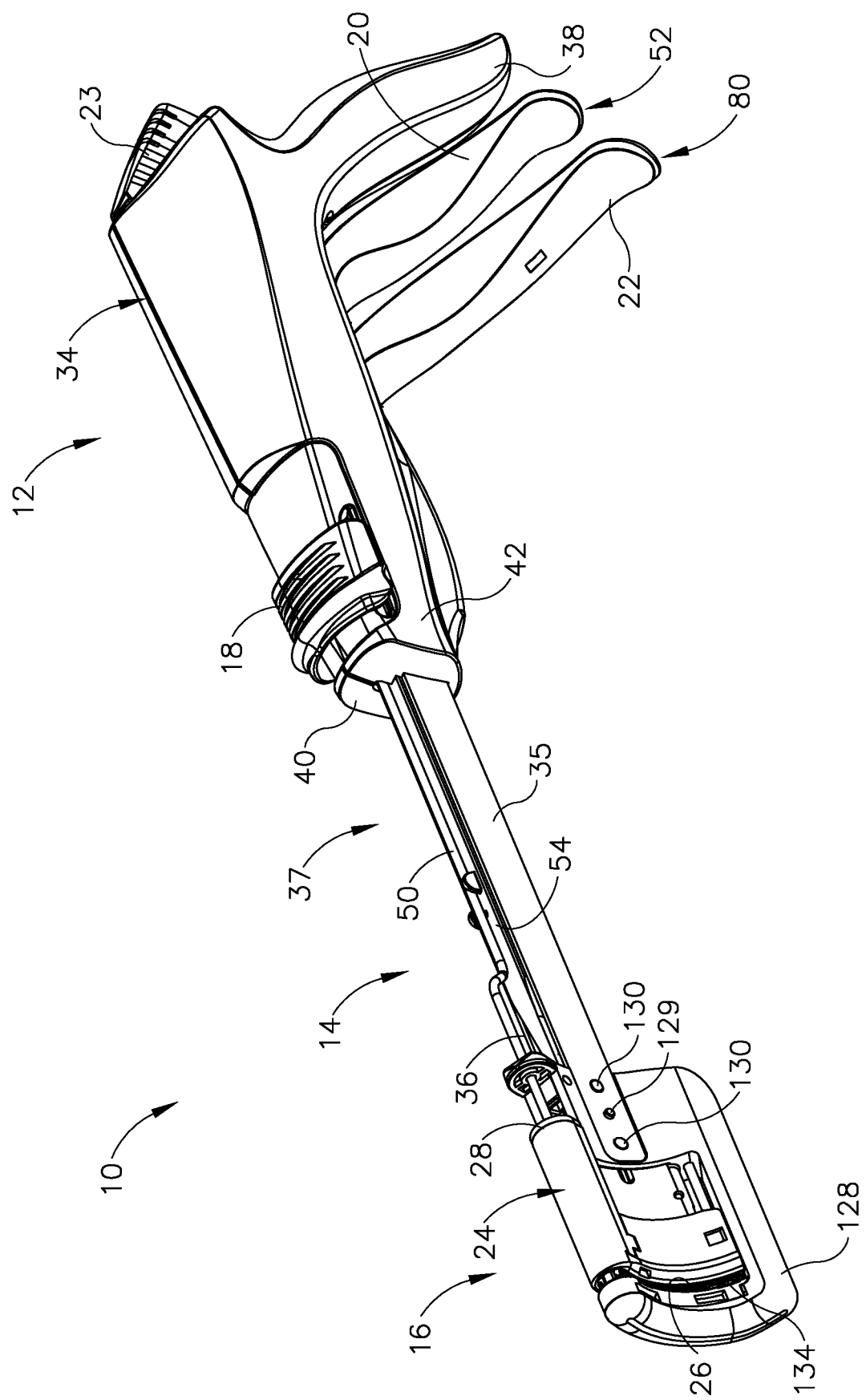
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). FIG. 1A shows slide (18) and closure trigger (20) in open configurations such that end effector (16) is configured to receive tissue laterally within a gap (25) of a replaceable cartridge unit (24) mounted within end effector (16), between an anvil (26) and a cartridge housing (28) of cartridge unit (24). As described in greater detail below, translating slide (18) distally toward end effector (16) slides a retaining pin (30) of end effector (16) distally, as shown in FIG. 1B, for capturing the tissue between anvil (26) and cartridge housing (28). As shown in FIGS. 1C and 1D, sequentially actuating closure trigger (20) and firing trigger (22) respectively compresses the tissue between anvil (26) and cartridge housing (28) in a closed configuration, and then forms a plurality of staples (not shown) within the tissue and severs the tissue with a curved knife (32) (see FIG. 6).

A. Handle Assembly and Shaft Assembly of Surgical Stapler

As shown in FIG. 1A, handle assembly (12) of surgical stapler (10) includes a handle housing (34) and a pair of handle frame plates (35, 36) having proximal portions (not shown) housed within handle housing (34) and elongate distal portions that extend distally along shaft assembly (14). As briefly described above, handle assembly (12) further includes saddle shaped slide (18), closure trigger (20), and firing trigger (22). Handle housing (34) defines a hand grip (38), which the operator may grasp with the palm of at least one hand. Handle housing (34) of the present example is formed by a right shroud handle portion (40) and a left shroud handle portion (42). Closure trigger (20) is proximally positioned relative to firing trigger (22), and each trigger (20, 22) is pivotally mounted to frame plates (35, 36) and are exposed through an underside of handle housing (34) to be manipulated by the fingers of the operator. FIG. 1A shows closure and firing triggers (20, 22) in unactuated positions prior to the closing of end effector (16) and firing of staples (not shown) and curved knife (32). Accordingly, cartridge housing (28) is spaced from anvil (26) for receiving tissue within gap (25) therebetween.

Surgical stapler (10) is operable to capture tissue via a tissue retaining pin actuation mechanism (37) prior to actuation of the closure and firing triggers (20, 22). Tissue retaining pin actuation mechanism (37) includes slide (18) of handle assembly (12), a tissue retaining pin (30) of end effector (16), and an elongate pushrod (50) of shaft assembly (14). Slide (18) is mounted on an upper surface of handle housing (34) and is configured to linearly translate between proximal and distal positions. Pushrod (50) operatively couples slide (18) with tissue retaining pin (30), such that longitudinal translation of slide (18) drives longitudinal actuation of tissue retaining pin (30) between a proximal open position (see FIG. 1A) and a distal closed position (see FIG. 1B), via pushrod (50).

Figure 2:
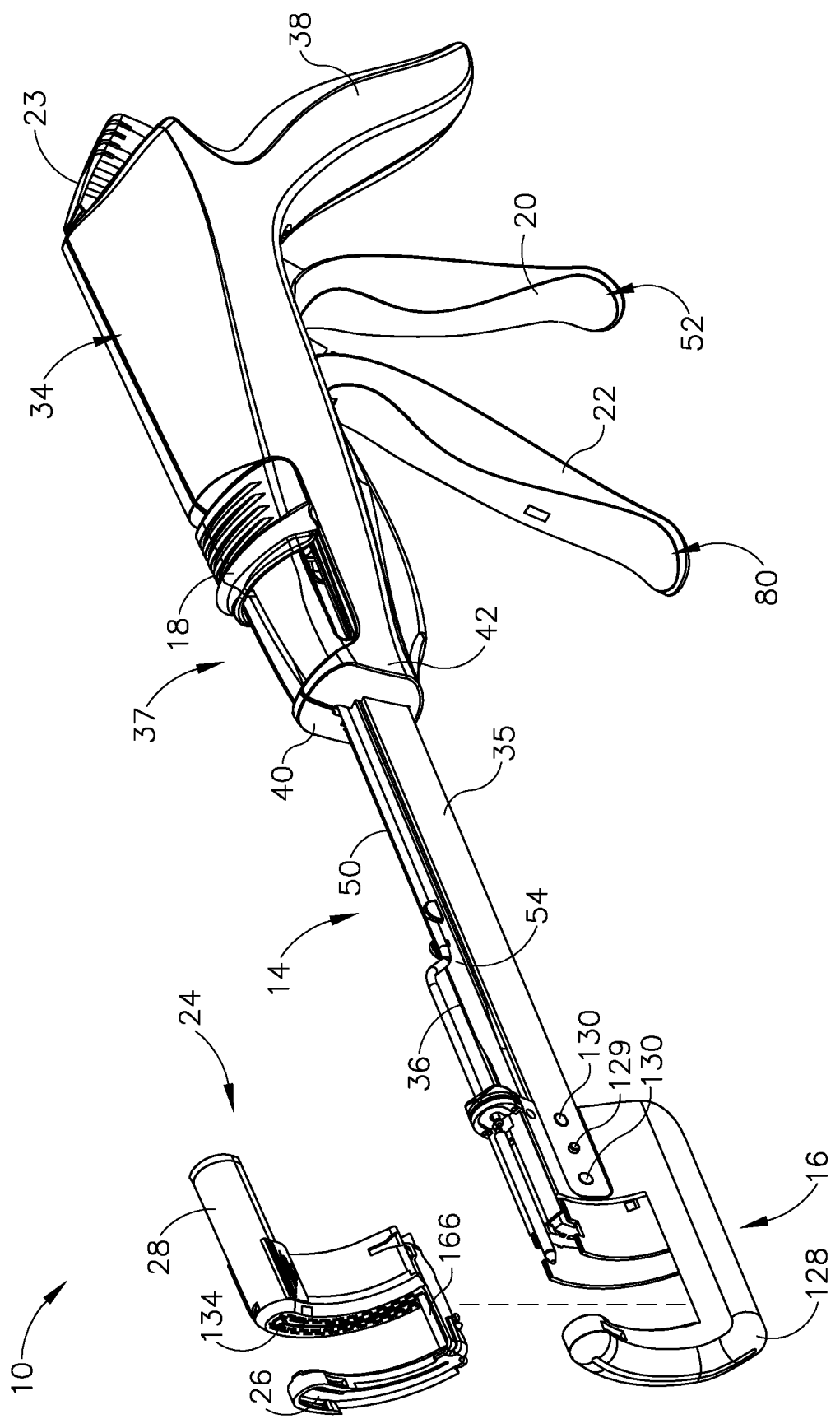
FIG. 2 depicts a partially exploded front perspective view of the surgical stapling instrument of FIG. 1A, showing the staple cartridge removed from a remainder of an end effector.

A closure mechanism (52) of surgical stapler (10) is configured to selectively actuate cartridge housing (28) of cartridge unit (24) between a proximal open position (FIG. 1A) and a distal closed position (FIG. 1C) for clamping tissue between cartridge housing (28) and anvil (26). Closure mechanism (52) includes closure trigger (20) of handle assembly (12) and an elongate closure member (54) coupled at its proximal end with closure trigger (20). Closure member (54) has a generally U-shaped cross-section and extends distally from handle assembly (12), through shaft assembly (14), and into end effector (16), such that a distal end of closure member (54) is configured to receive cartridge unit (24) within end effector (16), as shown in FIG. 2. A proximal end of closure member (54) is operatively connected with closure trigger (20) by a plurality of linkages (not shown) configured to convert pivoting motion of closure trigger (20) into translation of closure member (54). Accordingly, pivoting of closure trigger (20) toward pistol grip (38) to a closed position (FIG. 1C) drives closure member (54) distally, which in turn drives cartridge housing (28) distally toward anvil (26) for clamping tissue therebetween. Subsequently, pivoting of closure trigger (20) away from pistol grip (38) to an open position (FIG. 1A) drives closure member (54) proximally, which in turn drives cartridge housing (28) proximally away from anvil (26) for releasing stapled tissue.

In some versions, closure member (54) may be further configured to cooperate with tissue retaining pin actuation mechanism (37) to automatically actuate retaining pin (30) distally to its closed position when the operator squeezes closure trigger (20). Such automation may be useful in the event that the operator did not manually actuate retaining pin (30) distally via slide (18) prior to squeezing closure trigger (20). Closure trigger (20) may be biased toward the open position by a resilient member (not shown) housed within handle housing (34).

A firing mechanism (80) of surgical stapler (10) is configured to actuate end effector (16) to staple and sever tissue clamped between anvil (26) and cartridge housing (28) in response to manipulation of firing trigger (22) of handle assembly (12). In that regard, firing mechanism (80) includes firing trigger (22), cartridge unit (24), and an elongate firing bar (not shown) that extends longitudinally through shaft assembly (14) and operatively couples firing trigger (22) with cartridge unit (24). Firing trigger (22) is positioned distally of closure trigger (20) such that firing trigger (22) may be pivoted closed only once closure trigger (20) has first been pivoted closed. Pivoting of firing trigger (22) from an open position (FIG. 1C) toward a closed (or "fired") position (FIG. 1D) drives the firing bar distally, which in turn drives internal components of cartridge housing (28) distally to thereby staple and sever the tissue clamped by end effector (16), as described in greater detail below.

One or both of closure trigger (20) and firing trigger (22) may be configured to releasably lock in one or more pivot positions, such as a fully closed position and/or one or more intermediate positions between fully open (i.e., unactuated) and fully closed (i.e., fully actuated), for example. Accordingly, and advantageously, the operator may release one or more hands from the trigger (20, 22) and hand grip (38) to perform another task during the surgical procedure, while the trigger (20, 22) maintains its position. The operator may then release the trigger (20, 22) from its locked state by depressing a release button (23) arranged on a proximal end of handle assembly (12).

Though not shown, shaft assembly (14) of surgical stapler (10) may include various additional components, such as an articulating joint, or may include a rearrangement of various components such that shaft assembly (14) may be modular relative to handle assembly (12).

B. End Effector of Surgical Stapler

Figure 3:
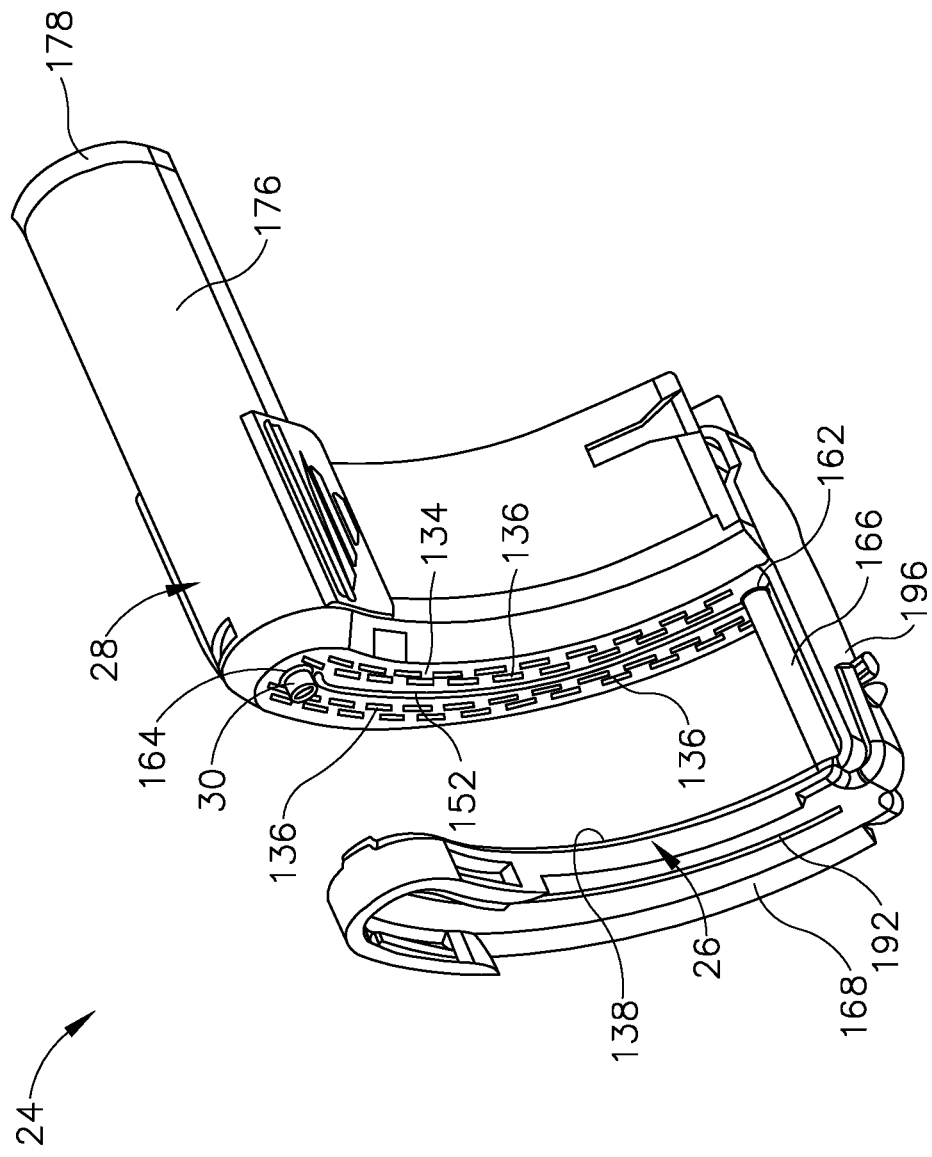
FIG. 3 depicts a front perspective view of the staple cartridge of FIG. 2.
Figure 4:
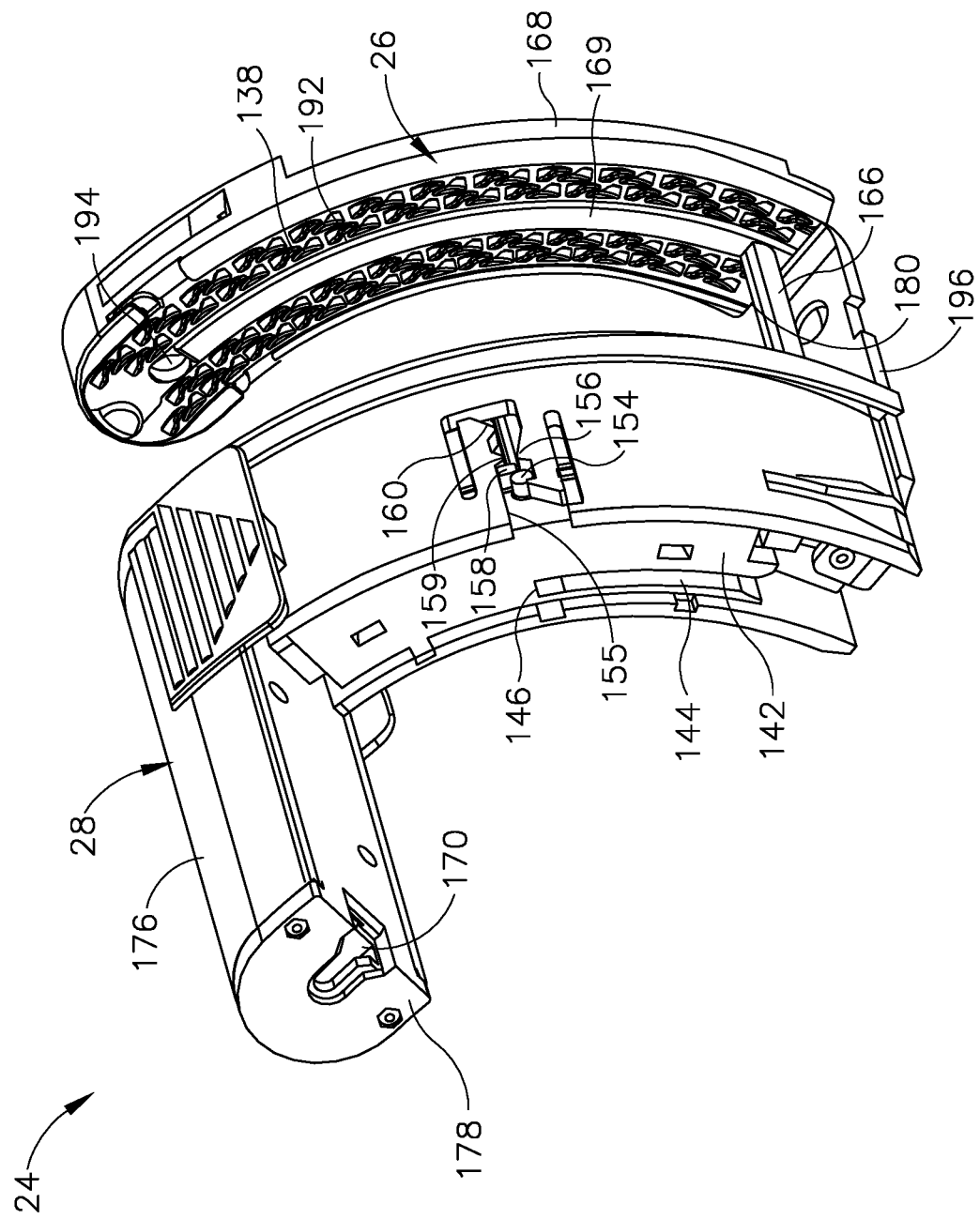
FIG. 4 depicts a rear perspective view of the staple cartridge of FIG. 2.
Figure 5:
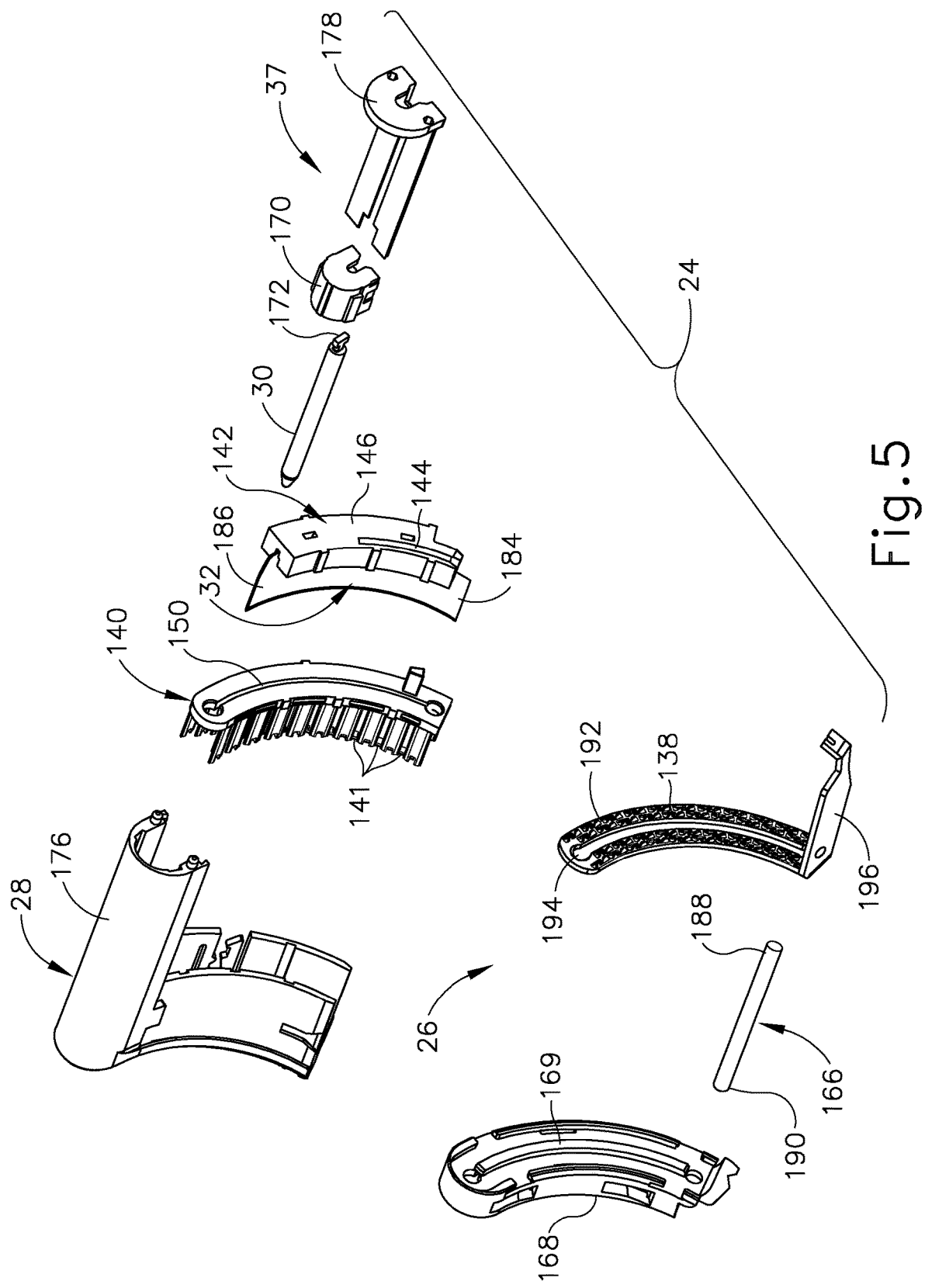
FIG. 5 depicts an exploded rear perspective view of the staple cartridge of FIG. 2.

As shown best in FIGS. 3-5, end effector (16) of the present example includes a C-shaped support structure (128) and replaceable cartridge unit (24) removably received by C-shaped support structure (128). Support structure (128) of the present example is secured to the distal ends of handle frame plates (35, 36) at the distal end of shaft assembly (14) by a shoulder rivet (129) and a pair of posts (130). The term "C-shaped" is used herein as reference to the curvature of support structure (128) and cartridge unit (24), each of which has a concave first lateral side and a convex second lateral side opposed from one another. Such a configuration provides enhanced functionality and access to tissue within the patient. By way of example only, the C-shaped construction of support structure (128) and cartridge unit (24) may enable end effector (16) to easily access the lower colon within the pelvic bowl of a patient, for example for performing a lower anterior resection ("LAR") in a proctocolectomy procedure. According, the term "C-shaped" as used herein should be construed to include a variety of concave shapes that would similarly enhance the functionality of surgical stapling and cutting instruments.

Replaceable cartridge unit (24) includes anvil (26) and cartridge housing (28), movably coupled to one another by a guide pin (166) and an anvil arm (196), as described in greater detail below. A distal end of cartridge housing (28) defines a distally facing staple deck (134) configured to contact tissue. Staple deck (134) includes a plurality of staple openings (136) arranged in staggered formation in a pair of rows on each side of an arcuate knife slot (152). Various other quantities of rows of staple openings (136) may be provided in other versions. Cartridge housing (28) houses a plurality of staples (not shown) configured to be driven distally through staple openings (136) and against anvil (26) to thereby form the staples in patient tissues. Though not shown, cartridge unit (134) may further include a retainer configured to removable couple to staple deck (134) to cover staple openings (136) and knife slot (152) before use of cartridge unit (24), for instance when cartridge unit (24) is stored, and optionally also after use of cartridge unit (24).

Figure 6:
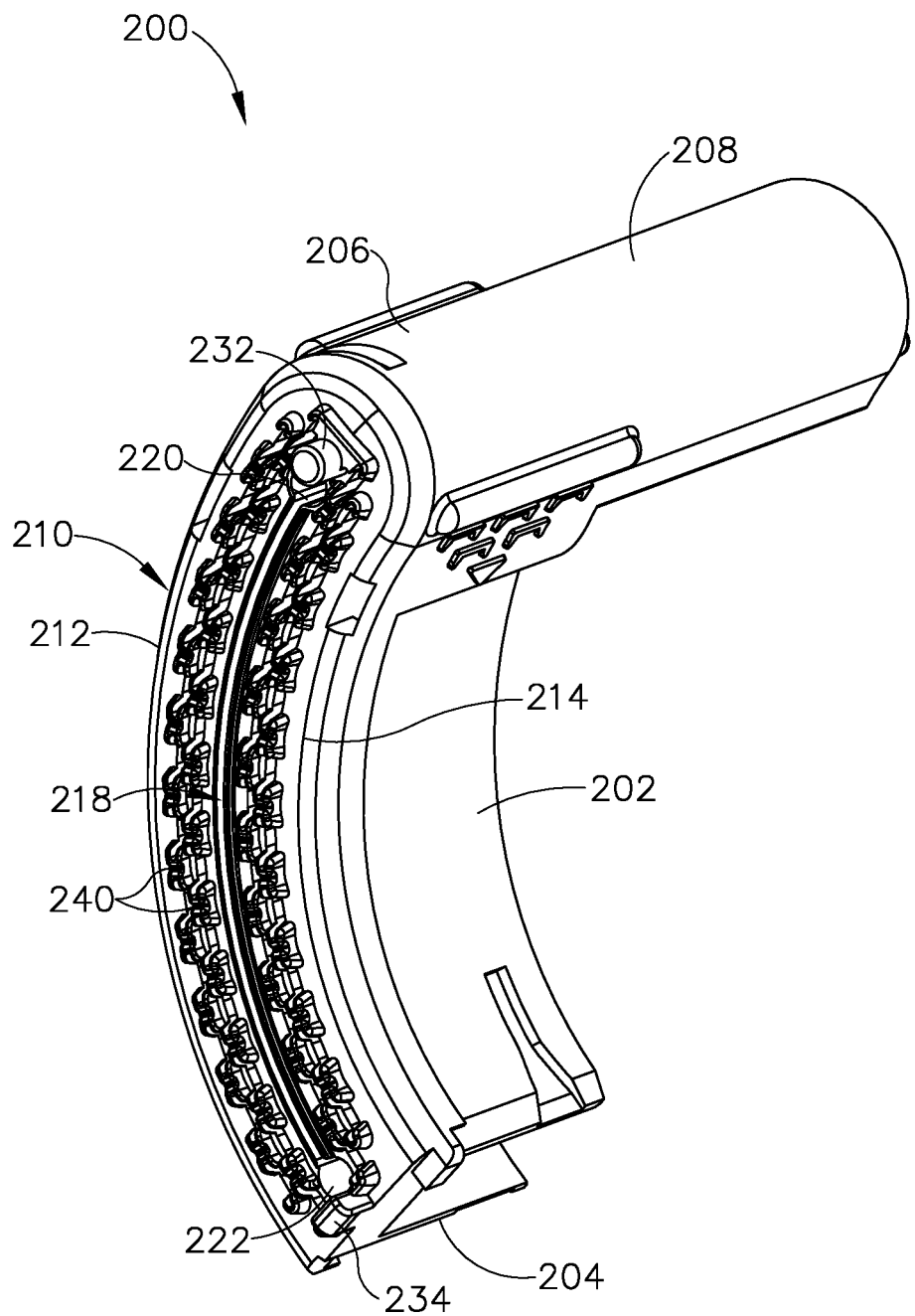
FIG. 6 depicts a front perspective view of another exemplary cartridge housing configured for use with the surgical stapling unit of FIG. 1A.

As shown in FIG. 6, cartridge housing (28) additionally houses retaining pin (30), a staple driver assembly (140), and a knife holder (142). Staple driver assembly (140) is positioned just proximally of the staples (not shown) housed within cartridge housing (28) and distally of knife holder (142). Staple driver assembly (140) of the present example is formed as a unitary structure defining a plurality of staple drivers (141). Thus, the term "assembly." as used in connection with staple driver assembly (140), is not intended to be limited to an assembly of individual components, but may also include integrally formed components with unitary structures. Driver assembly (140) is configured to translate distally within cartridge housing (28) so that staple drivers (141) drive staples distally from respective staple openings (136) and toward anvil (26) for formation within tissue clamped between anvil (26) and cartridge housing (28).

Knife holder (142) is movably disposed within cartridge housing (28) just proximally of staple driver assembly (140).

Knife holder (142) supports curved knife (32) along a distal side thereof, and knife holder (142) is configured to translate within cartridge housing (28) such that curved knife (32) extends distally through an arcuate slot (150) of driver assembly (140) and arcuate slot (152) of staple deck (134). A proximal side of knife holder (142) includes a slot (144) and a ledge (146) configured to couple with a knife retractor hook (not shown) for retraction of curved knife (32) after firing of cartridge unit (24), for example as disclosed in U.S. Pat. No. 10,045,780, entitled "Method of Applying Staples in Lower Anterior Bowel Resection," issued Aug. 14, 2018, the disclosure of which is incorporated by reference herein.

As shown in FIG. 4, a lateral side of cartridge housing (28) includes a longitudinally extending detent slot (155) defined between a confronting pair of resilient members. A first side of detent slot (155) includes a first proximal detent protrusion (156), and an opposed second side of detent slot (1.55) includes a second proximal detent protrusion (159) and a distal detent protrusion (160). Detent slot (155) is configured to slidably receive a detent post (154) of knife holder (142) and a detent post (158) of staple driver assembly (140). As staple driver assembly (140) and knife holder (142) translate distally within cartridge housing (28), detent post (154) resiliently engages detent protrusion (156), and detent post (158) resiliently engages detent protrusions (159, 160).

As shown in FIG. 3, cartridge housing (28) includes two longitudinally extending, generally circular holes (162, 164) at respective upper and lower ends of arcuate knife slot (152) on staple deck (134). Holes (162, 164) of the present example are positioned such that staple openings (136), and the staples ejected therefrom, extend beyond holes (162, 164) at the upper and lower ends of staple deck (134). Lower hole (162) is shaped and dimensioned to slidably receive a guide pin (166) that extends longitudinally between cartridge housing (28) and anvil (26). Upper hole (164) is shaped and dimensioned to slidably receive retaining pin (30) therethrough, such that retaining pin (30) may actuate longitudinally relative to cartridge housing (28) and anvil (26) between the proximal retracted position (FIG. 1A) and the distal extended position (FIG. 1B).

As shown in FIG. 5, a proximal end of retaining pin (30) includes a first coupling feature (172) (e.g., a projection) configured to couple with a corresponding coupling feature (not shown) (e.g., a groove) of a couplet (170), so that retaining pin (30) is secured to couplet (170). Couplet (170) and retaining pin (30) are slidably disposed within an upper arm (176) of cartridge housing (28), and are captured proximally therein by an end cap (178) secured to upper arm (176) proximally of couplet (170). A distal end of pushrod (50) of tissue retaining pin actuation mechanism (37), described above, is operatively coupled with couplet (170). Accordingly, longitudinal actuation of pushrod (50) via slide (18) of handle assembly (12) drives couplet (170) and thus retaining pin (30) longitudinally relative to cartridge housing (28) for capturing tissue to be stapled by end effector (16).

Anvil (26) of the present example includes a plastic cutting washer (168) and a metallic staple-forming surface (138) secured to a proximal side of cutting washer (168). Staple-forming surface (138) includes an elongate arcuate slot (192) configured to receive an arcuate projection (169) of cutting washer (168) therethrough to secure staple-forming surface (138) relative to cutting washer (168). Staple-forming surface (138) further includes a plurality of pockets arranged in rows along either side of arcuate slot (192). These pockets are configured to receive and form the legs of staples driven distally from staple openings (136) of staple deck (134). Accordingly, anvil (26) is spaced distally from and is aligned with staple deck (134) such that each pocket of staple-forming surface (138) aligns with a respective staple opening (136).

Staple-forming surface (138) of anvil (26) further includes a first circular opening (194) disposed at an upper end of arcuate slot (192), and a second circular opening (see FIG. 4) disposed at a lower end of arcuate slot (192). First opening (194) is configured to slidably receive a pointed distal tip of tissue retaining pin (30) when tissue retaining pin (30) is actuated distally to capture tissue positioned between anvil (26) and cartridge housing (28), The lower second opening of staple-forming surface (138) receives a distal end (190) of guide pin (166) therethrough, which extends into and fixedly couples to a lower end of cutting washer (168), such that guide pin (166) is longitudinally fixed relative to anvil (26).

A proximal end (188) of guide pin (166) is slidably received through lower hole (162) formed in staple deck (134) of cartridge housing (28), as described above. An anvil arm (196) projecting proximally from a lower end of staple-forming surface (138) is movably received through an open lower end of cartridge housing (28) to thereby trap proximal end (188) of guide pin (166) within cartridge housing (28), while still permitting cartridge housing (28) to actuate toward anvil (26). Accordingly, cartridge housing (28) is configured to slide longitudinally along guide pin (166) (and tissue retaining pin (30)) relative to anvil (26) in response to actuation of closure trigger (20), described above. As shown in FIG. 4, an interior side of guide pin (166) includes a longitudinal slot (180) configured to slidably receive a corresponding lower end (184) of curved knife (32) as cartridge housing (28) actuates longitudinally relative to anvil (26). An interior side of tissue retaining pin (30) may include a similar longitudinal slot (not shown) configured to slidably receive a corresponding upper end (186) of curved knife (32) as cartridge housing (28) actuates longitudinally relative to anvil (26).

C. Exemplary Actuation of Surgical Stapler

Having described various structural features of surgical stapler (10) above, including cartridge unit (24), exemplary actuation of surgical stapler (10) during a surgical procedure will now be described below. Surgical stapler (10) is first suitably manipulated within a body cavity of a patient to position patient tissue within gap (25) (see FIG. 1A) between anvil (26) and cartridge housing (28). As shown in FIG. 1B, slide (18) is then actuated distally to drive pushrod (50) distally, thereby driving tissue retaining pin (30) distally from cartridge housing (28) toward anvil (26). The pointed distal tip of tissue retaining pin (30) securely engages (e.g., pierces) the tissue and thereby captures the tissue within gap (25).

As shown in FIG. 1C, closure trigger (20) is then squeezed toward pistol grip (38) to drive closure member (54) distally, thereby driving cartridge housing (28) distally toward anvil (26) along tissue retaining pin (30) and guide pin (166) to clamp the tissue between cartridge deck (134) and anvil (26). Cartridge housing (28) may be maintained in this closed position relative to anvil (26) by an internal locking mechanism (not shown) of handle assembly (12) that holds closure trigger (20) in the squeezed position, as described above. As shown in FIG. 1D, while cartridge unit (24) remains in this closed position, firing trigger (22) is then squeezed toward closure trigger (20) and pistol grip (38) to drive the elongate firing bar (not shown) distally, thereby driving staple driver assembly (140) and knife holder (142) distally within cartridge housing (28). Stapler drivers (141)

of driver assembly (140) drive staples (not shown) distally through the captured tissue and against staple-forming surface (138) of anvil (26) to form the staples within the tissue and thereby fluidly seal the tissue. As the staples are being formed, curved knife (32) is driven distally by knife holder (142) through arcuate slots (150, 152) and into the clamped tissue to thereby sever the tissue along an arcuate path extending between the two innermost rows of the formed staples. Similar to closure trigger (20), firing trigger (22) may be held in its squeezed position by the internal locking mechanism (not shown) of handle assembly (12). It will be appreciated that surgical stapler (10) may be configured in some versions such that the tissue clamped by end effector (16) within gap (25) is stapled and cut simultaneously; and be alternatively configured in other versions such that the tissue is fully stapled and subsequently cut in sequential steps.

Once surgical stapler (10) has been fully fired into the patient tissue as described above, the operator may depress release button (23) of handle assembly (12) to release firing trigger (22) and closure trigger (20) from their squeezed positions. In this manner, curved knife (32) may be retracted proximally back into cartridge housing (28), and cartridge housing (28) may be retracted proximally along pins (20, 166) to thereby release the newly stapled and severed tissue from between anvil (26) and cartridge deck (134). The fired cartridge unit (24) may then be removed from support structure (128) of end effector (16), discarded, and replaced for further treatment if so desired.

Surgical stapler (10) may be further configured and operable in accordance with any of the teachings of the references cited herein, including U.S. Pat. No. 10,045,780, incorporated by reference above.

II. Exemplary Cartridge Housing Having Sloped Deck

In some instances, it may be desirable to provide a version of cartridge housing (28) that includes features that enhance gripping and stabilization of tissue during actuation of cartridge unit (24). Such a configuration may promote successful cutting and stapling of the tissue, and mitigate any damage caused to the tissue during such treatment. FIG. 6 shows an exemplary alternative cartridge housing (200) configured in such a manner, and which may be readily incorporated into cartridge unit (24) described above in place of cartridge housing (28). Cartridge housing (200) is configured and operable in a manner similar to cartridge housing (28), except as otherwise described below.

Cartridge housing (200) includes a curved body (202) that extends along an arcuate path and has an open lower body end (204), a closed upper body end (206), and an upper arm (208) extending proximally from upper body end (206). Curved body (202) and upper arm (208) of the present example have hollow interiors that communicate with one another and are configured to house respective moveable components similar to cartridge housing (28) described above. In particular, curved body (202) is configured to movably house staple driver assembly (140), a plurality of staples (not shown), knife holder (142), and curved knife (32), shown in FIG. 5. Upper arm (208) is configured to movably house tissue retaining pin (30) and couplet (170), which are retained within upper arm (208) by end cap (178), also shown in FIG. 5. Cartridge housing (200) is configured to couple with anvil (26) in a manner similar to cartridge housing (28) described above to define a cartridge unit similar to cartridge unit (24). The resulting cartridge unit is configured to be removably received by C-shaped support structure (128) of end effector (16) such that curved body (202) couples with the distal ends of frame plates (35, 36) of closure mechanism (52); such that couplet (170) couples with the distal end of pushrod (50) of tissue retaining pin actuation mechanism (37); and such that staple driver assembly (140) and knife holder (142) couple with the distal end of the firing bar (not shown) of firing mechanism (80).

A distal face of curved body (202) of cartridge housing (200) defines a distally-facing staple deck (210) that extends along the arcuate path of curved body (202) and has a first elongate side edge (212) that extends along a convex side of curved body (202), and an opposed second elongate side edge (214) that extends along a concave side of curved body (202). As described in greater detail below in connection with FIG. 10, staple deck (210) of the present example is sloped away from arcuate knife slot (218) in a downward direction toward deck side edges (212, 214). Similar to staple deck (134) described above, staple deck (210) is configured to clamp tissue against staple-forming surface (138) of anvil (26) when cartridge housing (200) is actuated distally toward anvil (26). Staple deck (210) includes a plurality of staple openings (216) configured to house a plurality of staples (not shown) that are driven distally through staple openings (216) by staple drivers (141) of staple driver assembly (140) for stapling clamped tissue in response to actuation of firing mechanism (80).

Figure 7:
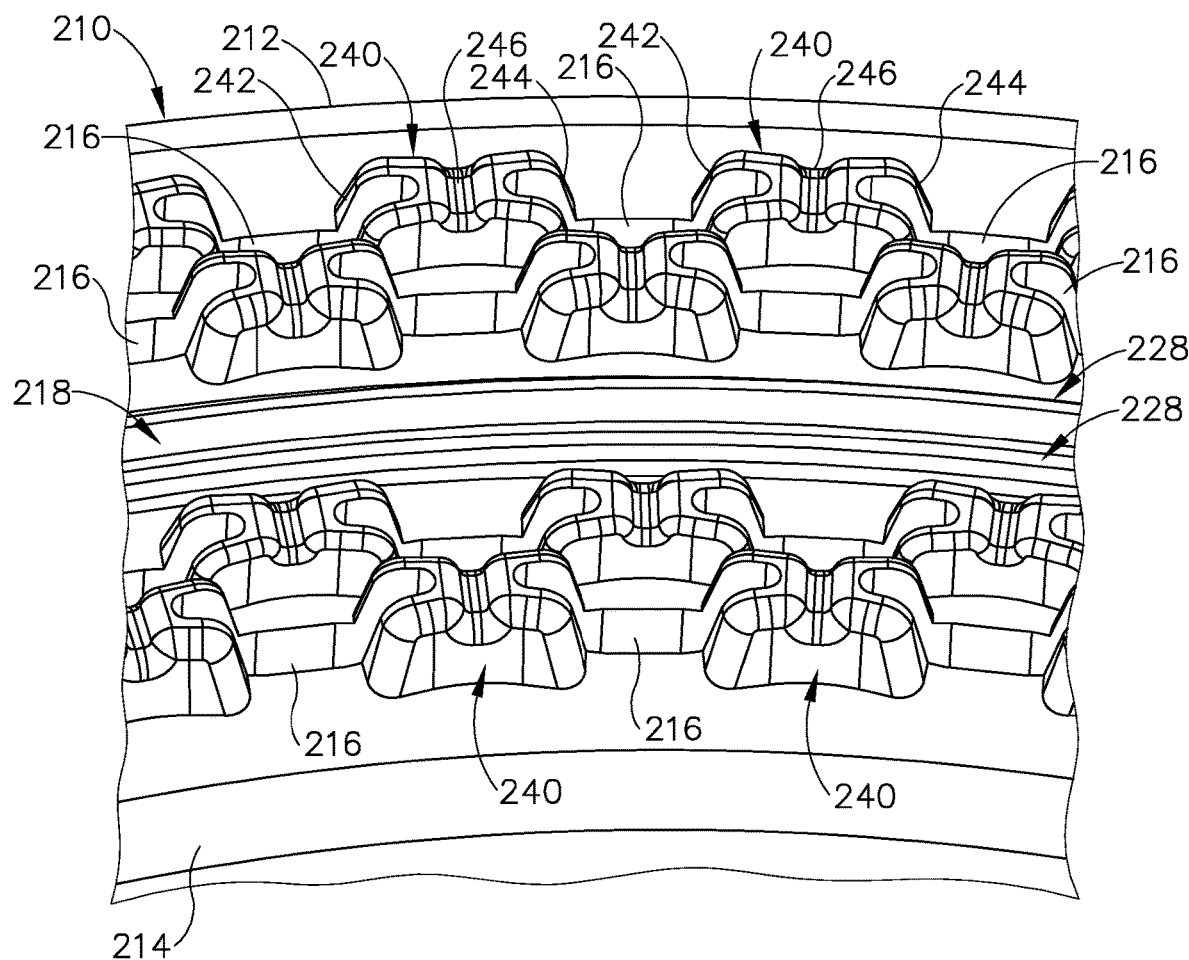
FIG. 7 depicts an enlarged perspective view of a medial portion of a deck of the cartridge housing of FIG. 6, showing details of tissue engagement features formed on the medial portion of the deck.

As shown best in FIG. 7, staple deck (210) further includes an arcuate knife slot (218) extending along an arcuate centerline of deck (210) so as to divide deck (210) into first and second elongate side portions. Arcuate knife slot (218) is configured to slidably receive curved knife (32) distally therethrough for cutting clamped tissue in response to actuation of firing mechanism (80). Staple openings (216) are arranged in a plurality of rows extending along arcuate paths parallel to arcuate knife slot (218) on the first and second side portions of deck (210). In the present version, each side portion of deck (210) includes an inner row and an outer row of staple openings (216), such that two rows of staple openings are arranged on each side of arcuate knife slot (218). Staple openings (216) of adjacent inner and outer rows are arranged in a staggered formation relative to one another. It will be appreciated that staple openings (216) may be arranged in various other row quantities and configurations in other versions.

Figure 8:
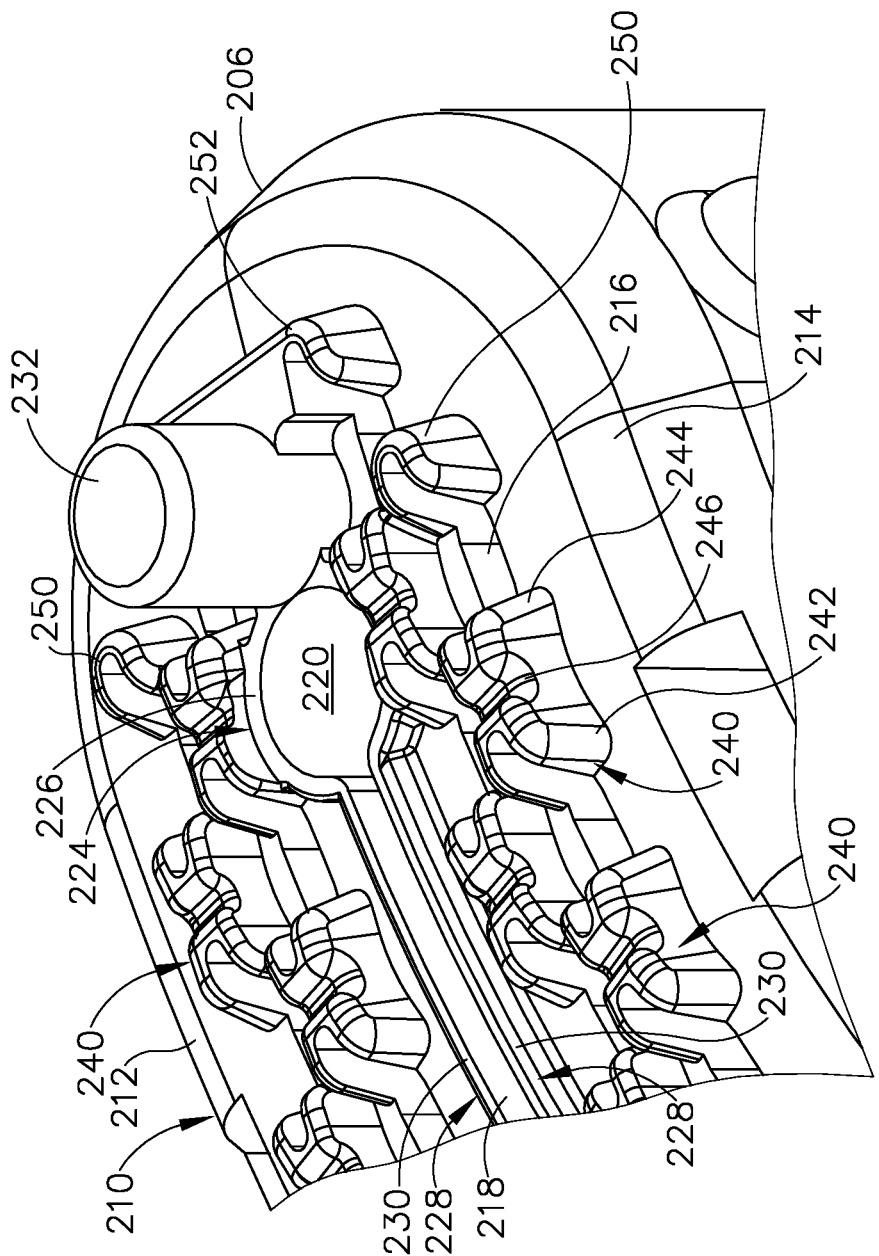
FIG. 8 depicts an enlarged perspective view of a first end portion of the deck of the cartridge housing of FIG. 6, showing details of tissue engagement features formed on the first end portion of the deck.

As shown best in FIG. 8, staple deck (210) further includes a first circular opening (220) arranged at a first end of arcuate knife slot (218) adjacent to upper body end (206). First circular opening (220) is aligned with and communicates directly with the first end of arcuate knife slot (218), and is configured to slidably receive tissue retaining pin (30) (see FIG. 5) therethrough. An end pair of staple openings (216) extends beyond first circular opening (220) in a direction toward upper body end (206). Accordingly, and advantageously, the staples ejected by the end pair of staple openings (216) are formed in tissue such that a hole formed in the tissue by tissue retaining pin (30) exhibits little to no leakage of fluid before a subsequent adjacent line of staples is applied to the tissue. As shown best in FIG. 9, staple deck (210) further includes a second circular opening (222) arranged at a second end of arcuate knife slot (218) adjacent to lower body end (204). Second circular opening (222) is aligned with and communicates directly with the second end of arcuate knife slot (218), and is configured to receive a proximal portion of guide pin (166) (see FIG. 5) therethrough.

Figure 9:
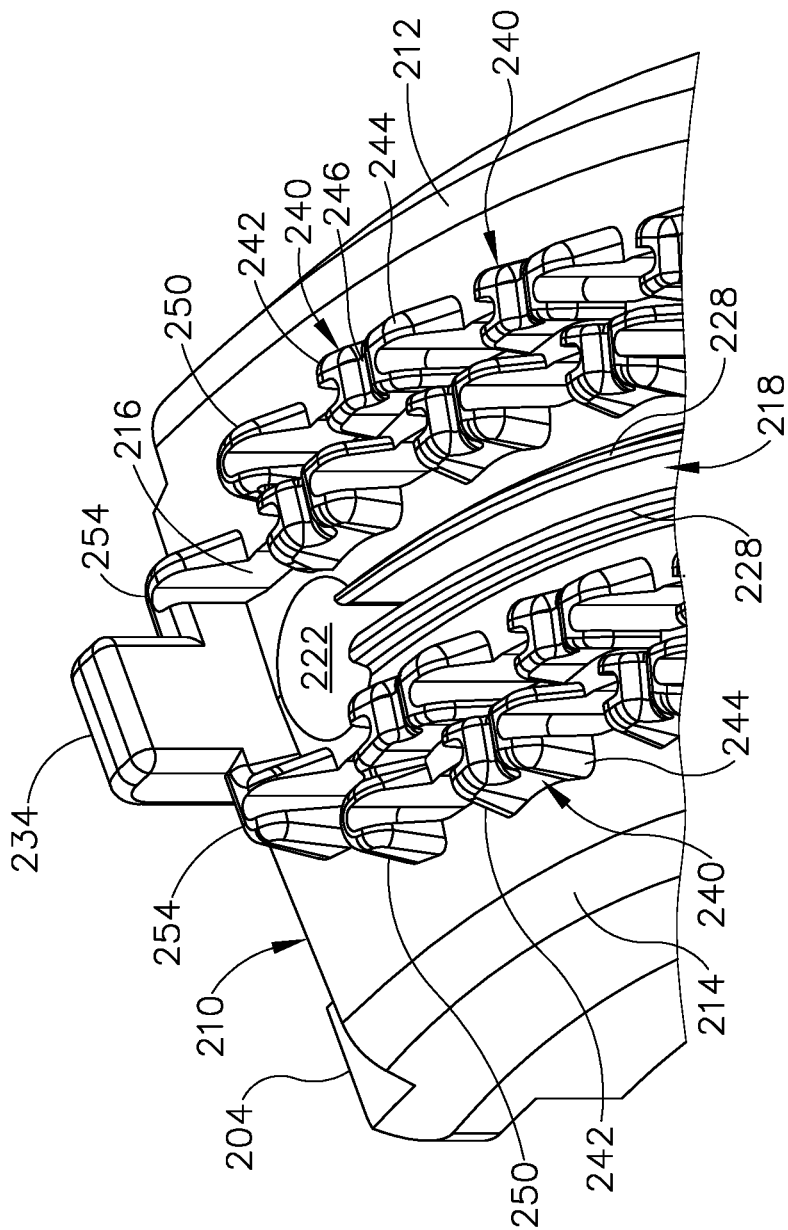
FIG. 9 depicts an enlarged perspective view of an opposed second end portion of the deck of the cartridge housing of FIG. 6, showing details of tissue engagement features formed on the second end portion of the deck.

As shown in FIG. 8, staple deck (210) of the present example further includes an annular wall (224) that substantially encircles first circular opening (220) and protrudes away from deck (210) to define a raised annular surface (226) offset from deck (210). In the present example, annular wall (224) is integrally connected with an adjacent pair of cleats (240), described below, disposed on opposed lateral sides of annular wall (224). Deck (210) further includes a pair of elongate ridges (228) that extend along opposing sides of arcuate knife slot (218) and project away from deck (210) to define raised ridge surfaces (230). Raised ridge surfaces (230) interconnect flush with raised annular surface (226) of annular wall (224) at the corresponding first end of arcuate knife slot (218). Elongate ridges (228) terminate at the opposed second end of arcuate knife slot (218), as shown in FIG. 9. Raised annular surface (226) is configured to clamp tissue against anvil (26) and thereby fix the tissue relative to first circular opening (220) to minimize tissue flow around tissue retaining pin (30) during cutting and stapling of tissue, and during subsequent proximal retraction of tissue retaining pin (30) into cartridge housing (200). Similarly, raised ridge surfaces (230) are configured to clamp tissue against anvil (26) and thereby fix the tissue relative to arcuate knife slot (218) to minimize tissue flow around knife slot (218) during cutting and stapling of the tissue.

As shown in FIGS. 6 and 8, a tissue gap post (232) is disposed on staple deck (210) just beyond first circular opening (220) in a direction toward upper body end (206), and in alignment with first circular opening (220) and arcuate knife slot (218). Tissue gap post (232) projects away from deck (210) and is configured to abut a first end of anvil (26) when cartridge housing (200) is driven distally against anvil (26). In this manner, tissue gap post (232) defines a minimum tissue gap between staple deck (210) and staple-forming surface (138) of anvil (26).

As shown in FIGS. 6 and 9, a tissue stop tab (234) is disposed on staple deck (210) just beyond second circular opening (222) in a direction toward lower body end (204), and in alignment with second circular opening (222) and arcuate knife slot (218). Tissue stop tab (234) projects away from deck (210) and functions as a stop feature that prevents tissue from flowing beyond lower body end (204) during cutting and stapling of the tissue. In some versions, tissue stop tab (234) is further configured to abut a second end of anvil (26) when cartridge housing (200) is driven distally, such that tissue stop tab (234) cooperates with tissue gap post (232) to define the minimum tissue gap between staple deck (210) and staple-forming surface (138) of anvil (26).

As shown in FIGS. 7-9, staple deck (210) of cartridge housing (200) further includes a plurality of tissue engagement features in the form of stand-off members (240, 250, 252, 254) that project away from deck (210). Stand-off members (240, 250, 252, 254) are distributed along a length of deck (210) and are laterally offset from arcuate knife slot (218) to align with and open to a respective one or more staple openings (216). As described below, stand-off members (240, 250, 252, 254) are configured to grip and thereby stabilize tissue when deck (210) is clamped against anvil (26); and, moreover, optimize tissue compression at the staple locations to facilitate effective stapling and cutting of the tissue.

As shown best in FIG. 7, a first set of stand-off members on staple deck (210) is shown in the form of cleats (240) arranged discretely along the length of arcuate knife slot (218) in alignment with staple openings (216). Each cleat (240) includes a first end feature (242) that wraps partially around an end portion of a first staple opening (216) within a given row of staple openings (216), and an opposed second end feature (244) that wraps partially around an end portion of an adjacent second staple opening (216) within the row of staple openings (216). First and second end features (242, 244) are integrally connected by a recessed bridge portion (246).

Each end feature (242, 244) of a cleat (240) is generally U-shaped and defines an inner wall that joins with and protrudes outwardly from an inner wall of the respective staple opening (216). In this manner, each end feature (242, 244) opens to and communicates with a respective staple opening (216). Accordingly, each end feature (242, 244) is configured to guide a respective staple leg of a corresponding staple (not shown) as the staple is ejected distally from the staple opening (216) by a staple driver (141). Each end feature (242, 244) thus cooperates with a confronting end feature (242, 244) of an adjacent cleat (240), or with an endcap (250, 252, 254) described below, to provide such guidance of the staples. In the present version, the lateral side of each end feature (242, 244) that laterally confronts an end feature (242, 244) of an adjacent row of cleats (240) is formed with a reduced wall thickness relative to an opposed lateral side of the same end feature (242, 244).

While cleats (240) of the present example are discretely formed relative to one another such that each cleat (240) is freestanding and is spaced apart from adjacent cleats (240), in other examples cleats (240) may be interconnected with one another along one or more portions of staple deck (210).

As shown in FIGS. 8 and 9, staple deck (210) includes additional stand-off members in the form of outer row endcaps (250) disposed at both ends of the outer rows of staple openings (216). In the present version, each outer row endcap (250) has a U-shape similar to end features (242, 244) of cleats (240), and wraps partially around an end portion of a respective staple opening (216) at the end of a respective outer row of staple openings (216). Accordingly, each outer row endcap (250) cooperates with a confronting end feature (242, 244) of an adjacent cleat (240) within the same row to guide a respective staple (not shown) distally into tissue as the staple is being ejected. In the present example, an inner surface of each outer row end cap (250) is integrally connected with an end feature (242, 244) of an adjacent cleat (240) of the adjacent inner row of cleats (240).

As shown in FIG. 8, a pair of first end inner row endcaps (252) is disposed at the ends of the inner rows of staple openings (216) at upper body end (206). First end inner row endcaps (252) of the present example are disposed on opposed lateral sides of tissue gap post (232) and are integrally joined with tissue gap post (232) (with only one endcap (252) being shown in FIG. 8). First end inner row endcaps (252) are otherwise similar to outer row endcaps (250) in that each endcap (252) has a U-shaped opening that wraps partially around an end portion of an end-most staple opening (216) and cooperates with a confronting end feature (242, 244) of a cleat (240) within the same row to guide a staple during distal ejection.

As shown in FIG. 9, a pair of second end inner row endcaps (254) is disposed at the ends of the inner rows of staple openings (216) at lower body end (204). Second end inner row endcaps (254) of the present example are disposed on opposed lateral sides of tissue stop tab (234) and are integrally joined with tissue stop tab (234). Second end inner row endcaps (254) are similar to outer row endcaps (250) in that each endcap (254) has a U-shaped opening that wraps partially around an end portion of an end-most staple opening (216) and cooperates with a confronting (242, 244) of a cleat (240) within the same row to guide a staple during distal ejection.

In the present example, cleats (240), outer row endcaps (250), and first end inner row endcaps (252) each protrude from deck (210) to thus collectively define and terminate at an upper plane. In contrast, second end inner row endcaps (254) each protrude from deck (210) so as to extend above the above the upper plane of members (240, 250, 252). Such configuration and corresponding advantages are disclosed in greater detail in U.S. patent application Ser. No. 16/234,727, entitled "Surgical Stapler with Tissue Engagement Features Around Tissue Containment Pin," filed Dec. 28, 2018, issued as U.S. Pat. No. 11,202,628 on Dec. 21, 2021, the disclosure of which is incorporated by reference herein.

Figure 10:
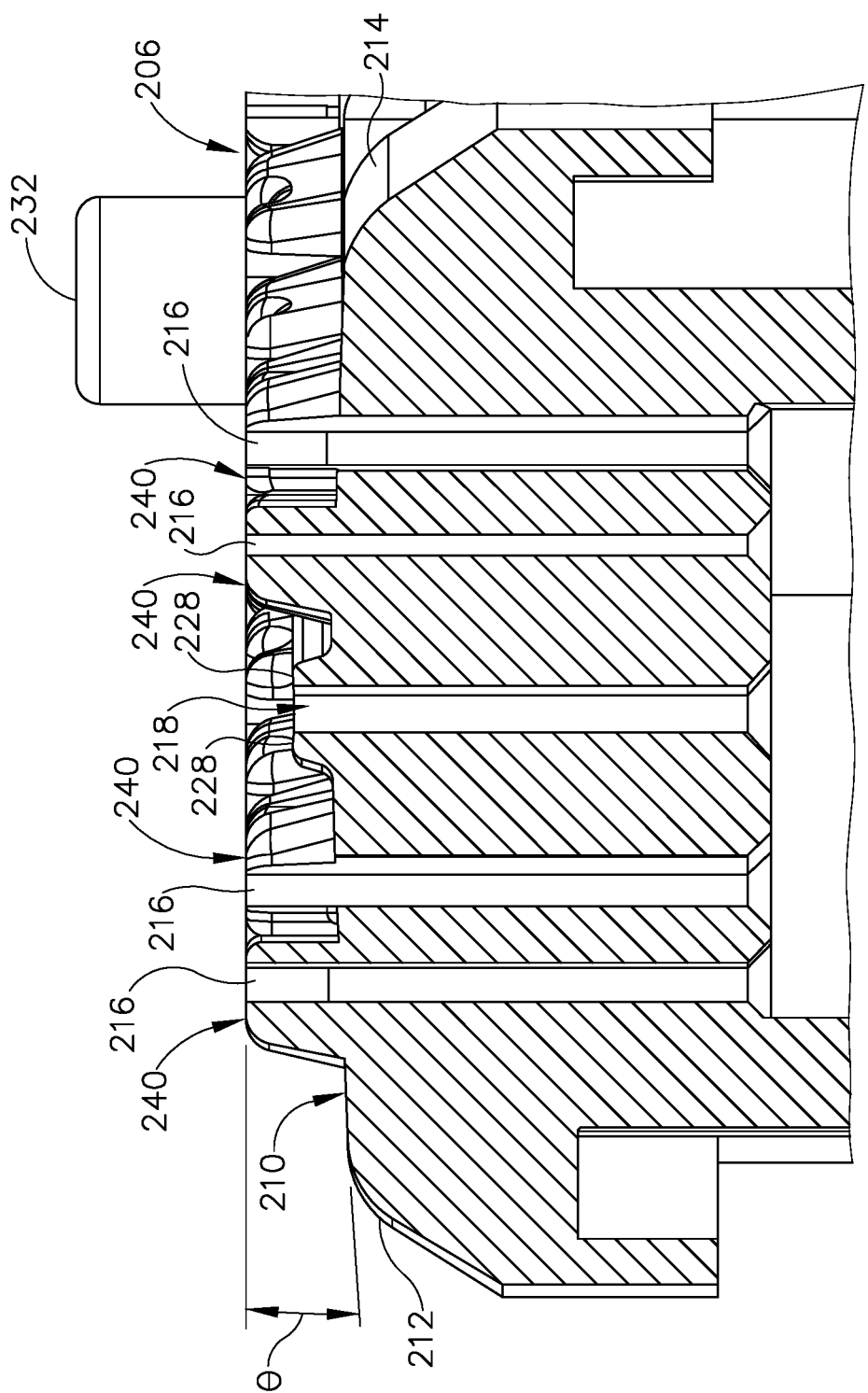
FIG. 10 depicts a cross-sectional view of the cartridge housing of FIG. 6, showing a sloped configuration of the deck.

As shown in FIG. 10, each side portion of staple deck (210) is sloped away from arcuate knife slot (218) in a downward direction toward the respective side edge (212, 214) of deck (210). Accordingly, an outermost portion of each deck side portion disposed laterally outward of cleats (240) is recessed below a corresponding innermost portion of the deck side portion disposed laterally inward of cleats (240), along a full length of arcuate knife slot (218). Furthermore, each side portion of deck (210) is uniformly sloped away from arcuate knife slot (218) at the same degree ($\theta$) relative to the upper plane defined by the upper surfaces of cleats (240), outer row endcaps (250), and first end inner row endcaps (252). In alternative versions, the first and second side portions of deck (210) may sloped downwardly away from arcuate knife slot (218) by differing degrees ($\theta$). Advantageously, the downwardly sloping configuration of the side portions of staple deck (210) provides varying compression of tissue across the lateral width of deck (210). In particular, a higher degree of tissue compression is applied near arcuate knife slot (218), and a lesser degree of compression is applied near deck side edges (212, 214). Accordingly, this sloped configuration of deck (210) cooperates with stand-off members (240, 250, 252, 254) to optimize tissue compression at the tissue cut line and at the staple locations to effectively stabilize the tissue during stapling and cutting, while minimizing tissue compression at deck side edges (212, 214) to prevent over-compression of tissue, as described further below.

It should be understood that the protruding configuration of stand-off members (240, 250, 252, 254) relative to deck (210) provides multiple advantages. In particular, when tissue is compressed between deck (210) and anvil (26) as described above, portions of the compressed tissue will enter the recessed areas in and around stand-off members (240, 250, 252, 254) (e.g., recessed bridge portions (246) and separation gaps). As a result of some tissue entering these recessed areas, tissue compression is optimized at the staple locations corresponding to stand-off members (240, 250, 252, 254) while the total pressure applied to the compressed tissue is decreased relative to a theoretical alternative configuration in which staple deck (210) is flat. By reducing the total pressure applied to the compressed tissue, the risk of damaging the tissue through over-compression is reduced. In addition to reducing the total pressure applied to the compressed tissue, the entry of tissue portions into the recessed areas in and around stand-off members (240, 250, 252, 254) provides an enhanced gripping effect on the compressed tissue that is enhanced relative to a theoretical alternative configuration in which staple deck (210) is flat. The enhanced gripping of tissue may promote cleaner cutting by knife (32) and more effective deployment of staples into the tissue. Thus, the provision of stand-off members (240, 250, 252, 254) may both reduce the risk of over-compression of tissue and promote greater success in cutting and stapling the tissue.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A cartridge for use with a surgical instrument, the cartridge comprising: (a) a curved body; (b) a deck defined by the curved body, wherein the deck is configured to clamp tissue against an anvil; (c) a plurality of staple openings formed in the deck, wherein the staple openings are configured to house a plurality of staples; and (d) an arcuate slot formed in the deck, wherein the arcuate slot is configured to slidably receive a cutting member therethrough, wherein the deck includes a sloped deck portion that slopes away from the arcuate slot in a direction transverse to a length of the arcuate slot, wherein the sloped deck portion is configured to provide varied compression of tissue across a width of the deck.

Example 2

The cartridge of Example 1, wherein the sloped deck portion extends along a full length of the arcuate slot.

Example 3

The cartridge of any of the preceding Examples, wherein at least some of the staple openings are arranged on the sloped deck portion.

Example 4

The cartridge of any of the preceding Examples, wherein the deck includes a first elongate side edge and an opposed second elongate side edge, wherein the sloped deck portion comprises: (i) a first side portion of the deck that slopes away from the arcuate slot in a direction toward the first elongate side edge, and (ii) a second side portion of the deck that slopes away from the arcuate slot in a direction toward the second elongate side edge.

Example 5

The cartridge of any of the preceding Examples, further comprising a plurality of stand-off members arranged on the deck, wherein the stand-off members are configured to engage tissue.

Example 6

The cartridge of Example 5, wherein at least some of stand-off members are arranged on the sloped deck portion.

Example 7

The cartridge of any Examples 5 through 6, wherein top surfaces of the stand-off members collectively define an upper plane, wherein the sloped deck portion is sloped relative to the upper plane.

Example 8

The cartridge of any of Examples 5 through 7, wherein the stand-off members are laterally offset from the arcuate slot.

Example 9

The cartridge of any of the preceding Examples, wherein each of the stand-off members wraps around at least a portion of an adjacent staple opening.

Example 10

The cartridge of any of the preceding Examples, wherein at least some of the stand-off members include a first end feature that wraps at least partially around an end portion of a first staple opening, and an opposed second end feature that wraps at least partially around an end portion of a second staple opening.

Example 11

The cartridge of Example 10, wherein the first end feature is connected with the second end feature by a recessed bridge portion.

Example 12

The cartridge of any of the preceding Examples, further comprising a pair of ridges extending along opposed sides of the arcuate slot.

Example 13

The cartridge of any of the preceding Examples, further comprising a circular opening formed in the deck adjacent to an end of the arcuate slot, wherein the circular opening is configured to slidably receive a pin therethrough.

Example 14

The cartridge of Example 13, wherein the circular opening communicates with the arcuate slot.

Example 15

The cartridge of any of Examples 13 through 14, wherein at least one of the staple openings extends beyond the circular opening in a direction toward a corresponding end of the deck.

Example 16

A cartridge for use with a surgical instrument, the cartridge comprising: (a) a curved body; (b) a deck defined by the curved body, wherein the deck is configured to clamp tissue against an anvil, wherein the deck includes a first elongate side edge and an opposed second elongate side edge; (c) an arcuate slot formed in the deck, wherein the arcuate slot extends along the deck and between the first and second elongate side edges, wherein the arcuate slot is configured to slidably receive a cutting member therethrough; and (d) a plurality of staple openings formed in the deck, wherein the staple openings are configured to house a plurality of staples, wherein a first row of the staple openings extends along the deck between the first elongate side edge and the arcuate slot, wherein a second row of the staple openings extends along the deck between the second elongate side edge and the arcuate slot, wherein a first outer portion of the deck extending between the first elongate side edge and the first row is recessed relative to a tissue contacting portion of the arcuate slot, wherein a second outer portion of the deck extending between the second elongate side edge and the second row is recessed relative to the tissue contacting portion of the arcuate slot.

Example 17

The cartridge of Example 16, wherein the deck comprises a first inner portion extending between the arcuate slot and the first row, and a second inner portion extending between the arcuate slot and the second row, wherein the first inner portion and the first outer portion slope away from the arcuate slot in a first direction, wherein the second inner portion and the second outer portion slope away from the arcuate slot in an opposed second direction.

Example 18

The cartridge of any of Examples 16 through 17, further comprising a plurality of stand-off members arranged on the deck and configured to engage tissue, wherein top surfaces of the stand-off members collectively define an upper plane, wherein the first outer portion and the second outer portion of the deck are sloped relative to the upper plane.

Example 19

A surgical instrument comprising: (a) a body; (b) a shaft assembly extending distally from the body; (c) an end effector at a distal end of the shaft assembly, wherein the end effector comprises: (i) a support structure, (ii) an anvil fixed relative to the support structure, wherein the anvil includes a plurality of staple-forming pockets, and (iii) a cartridge housing, wherein the cartridge housing is movable relative to the support structure to clamp tissue against the anvil, wherein the cartridge housing comprises: (A) a curved body, (B) a deck defined by the curved body, (C) a plurality of staple openings formed in the deck, wherein the staple openings are configured to house a plurality of staples, (D) an arcuate slot formed in the deck, wherein the arcuate slot is configured to slidably receive a cutting member therethrough, and (E) a plurality of stand-off members arranged on the deck along a length of the arcuate slot, wherein a side portion of the deck is sloped away from the stand-off members.

Example 20

The surgical instrument of Example 19, wherein the side portion of the deck is sloped away from the stand-off members in a direction transverse to the arcuate slot.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A cartridge for use with a surgical instrument, the cartridge comprising:
   (a) an elongate body;
   (b) a deck defined by the elongate body, wherein the deck includes an elongate side edge and is configured to clamp tissue against an anvil;
   (c) a plurality of staple openings formed in the deck, wherein the staple openings are configured to house a plurality of staples;
   (d) a plurality of stand-off members arranged on the deck and configured to engage tissue; and
   (e) an elongate slot formed in the deck, wherein the elongate slot is configured to slidably receive a cutting member therethrough along a longitudinal axis that extends distally,
   wherein the deck includes a sloped deck portion that slopes away at a constant angle from the elongate slot to the elongate side edge along either side of an entire length of the elongate slot, wherein the sloped deck portion is configured to provide varied compression of tissue across a width of the deck, and
   wherein the stand-off members are disposed on the sloped deck portion and collectively terminate distally at a stand-off plane extending parallel to the longitudinal axis such that the stand-off members vary in height relative to the sloped deck portion along the width of the deck.

2. The cartridge of claim 1, wherein each of the stand-off members includes a height that extends from the sloped deck portion to the stand-off plane.

3. The cartridge of claim 1, wherein at least some of the staple openings are arranged on the sloped deck portion.

4. The cartridge of claim 1, wherein the deck includes a first elongate side edge and an opposed second elongate side edge, wherein the sloped deck portion comprises:
   (i) a first side portion of the deck that slopes away from the elongate slot in a direction toward the first elongate side edge, and
   (ii) a second side portion of the deck that slopes away from the elongate slot in a direction toward the second elongate side edge.

5. The cartridge of claim 4, wherein the first side portion of the deck includes a first slope, and the second side portion of the deck includes a second slope.

6. The cartridge of claim 5, wherein the first slope includes a first angle, and the second slope includes a second angle, wherein the first angle is sloped a same number of degrees relative to the second angle, wherein the first slope is in an opposite direction as the second angle.

7. The cartridge of claim 1, wherein the elongate body includes a curved body and the elongate slot includes an arcuate slot.

8. The cartridge of claim 1, wherein the stand-off members are laterally offset from the elongate slot.

9. The cartridge of claim 1, wherein each of the stand-off members extends around at least a portion of an adjacent staple opening.

10. The cartridge of claim 1, wherein at least some of the stand-off members include a first end feature that wraps at least partially around an end portion of a first staple opening, and an opposed second end feature that wraps at least partially around an end portion of a second staple opening.

11. The cartridge of claim 10, wherein the first end feature is connected with the second end feature by a recessed bridge portion.

12. The cartridge of claim 1, further comprising a pair of ridges extending along opposed sides of the elongate slot.

13. The cartridge of claim 1, further comprising a circular opening formed in the deck adjacent to an end of the elongate slot, wherein the circular opening is configured to slidably receive a pin therethrough.

14. The cartridge of claim 13, wherein the circular opening communicates with the elongate slot.

15. The cartridge of claim 13, wherein at least one of the staple openings extends beyond the circular opening in a direction toward a corresponding end of the deck.

16. A cartridge for use with a surgical instrument, the cartridge comprising:
   (a) a curved body;
   (b) a deck defined by the curved body, wherein the deck is configured to clamp tissue against an anvil, wherein the deck includes a first elongate side edge and an opposed second elongate side edge;
   (c) an arcuate slot formed in the deck, wherein the arcuate slot extends along the deck and between the first and second elongate side edges, wherein the arcuate slot is configured to slidably receive a cutting member therethrough;
   (d) a plurality of staple openings formed in the deck, wherein the staple openings are configured to house a plurality of staples, wherein a first row of the staple openings extends along the deck between the first elongate side edge and a first side of the arcuate slot, wherein a second row of the staple openings extends along the deck between the second elongate side edge and a second side of the arcuate slot; and
   (e) a plurality of stand-off members distributed among the plurality of staple openings, wherein the stand-off members collectively terminate distally at a stand-off plane parallel to a length of the arcuate slot,
   wherein the deck slopes downwardly away from the arcuate slot towards the first elongate side edge on the first side of the arcuate slot and the deck slopes downwardly away from the arcuate slot towards the second elongate side edge on the second side of the arcuate slot.

17. The cartridge of claim 16, wherein the deck further includes elongate ridges that extend along the first and second sides of the arcuate slot.

18. The cartridge of claim 17, wherein the stand-off plane is spaced away from the deck by a distance that is greater than a maximum height of the elongate ridges relative to the deck.

19. A surgical instrument, comprising:
   (a) a body;
   (b) a shaft extending distally from the body; and
   (c) an end effector at a distal end of the shaft, wherein the end effector comprises:
      (i) a support structure,
      (ii) an anvil fixed relative to the support structure, wherein the anvil includes a plurality of staple-forming pockets, and
      (iii) a cartridge housing, wherein the cartridge housing is movable relative to the support structure to clamp tissue against the anvil, wherein the cartridge housing comprises:
         (A) a curved body,
         (B) a deck defined by the curved body and including a first side portion and a second side portion,
         (C) a plurality of staple openings formed in the deck, wherein the staple openings are configured to house a plurality of staples,
         (D) an arcuate slot formed in the deck, wherein the arcuate slot is configured to slidably receive a cutting member therethrough, wherein the arcuate slot separates the first side portion from the second side portion,
         (E) first and second elongate ridges extending along opposed first and second sides, respectively, of the arcuate slot, and
         (F) a plurality of stand-off members arranged on the deck along an entire length of the arcuate slot, wherein the stand-off members collectively define a plane extending parallel to a length of the arcuate slot,
      wherein the first side portion of the deck defines a first deck plane that slopes downwardly from the first elongate ridge in a direction away from the arcuate slot.

20. The surgical instrument of claim 19, wherein the second side portion defines a second deck plane that slopes downwardly from the second elongate ridge in a direction away from the arcuate slot.

* * * * *